(12) United States Patent
Flaherty et al.

(10) Patent No.: US 7,729,738 B2
(45) Date of Patent: *Jun. 1, 2010

(54) STABILIZED TISSUE PENETRATING CATHETERS

(75) Inventors: J. Christopher Flaherty, Los Altos, CA (US); Joshua Makower, Los Altos, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 1883 days.

This patent is subject to a terminal disclaimer.

(21) Appl. No.: 10/773,836

(22) Filed: Feb. 5, 2004

(65) Prior Publication Data

US 2004/0158143 A1 Aug. 12, 2004

Related U.S. Application Data

(63) Continuation-in-part of application No. 09/282,774, filed on Mar. 31, 1999, now Pat. No. 6,375,615, application No. 10/773,836, which is a continuation-in-part of application No. 08/837,294, filed on Apr. 11, 1997, now Pat. No. 6,302,875, and a continuation-in-part of application No. 09/179,809, filed on Oct. 27, 1998, now Pat. No. 6,068,638, which is a continuation of application No. 08/730,496, filed on Oct. 11, 1996, now Pat. No. 5,830,222.

(60) Provisional application No. 60/005,164, filed on Oct. 13, 1995, provisional application No. 60/010,613, filed on Feb. 2, 1996, provisional application No. 60/080,196, filed on Mar. 31, 1998.

(51) Int. Cl.
*A61B 5/05* (2006.01)

(52) U.S. Cl. .................. 600/407; 600/424; 604/20; 604/21; 604/41; 604/96.01; 604/98.02; 604/159; 604/528; 604/529; 604/530

(58) Field of Classification Search ............. 600/407, 600/424; 604/20–21, 41, 96.01–98.02, 159, 604/528–530
See application file for complete search history.

(56) References Cited

U.S. PATENT DOCUMENTS 4,950,267 A * 8/1990 Ishihara et al. ............. 606/12

(Continued)

OTHER PUBLICATIONS

New Approaches and Conduits: in Situ Venous Arterialization and Coronary Artery Bypass; Peter J. Fitzgerald, et al.;Curent Interventional Cardiology Reports 1999; Current Science Inc.

*Primary Examiner*—Brian Casler
*Assistant Examiner*—James Kish

(57) ABSTRACT

A tissue penetrating catheter that is usable to advance a tissue penetrator from within a blood vessel, through the wall of the blood vessel to a target location. The catheter includes at least one stabilizing device thereon for stabilizing catheter prior to advancing the tissue penetrator. The tissue penetrator may extend through a lumen in the body of the catheter and project transversely through an exit port. The stabilizing device may be located closely adjacent to the exit port, or may surround the exit port. The stabilizing device may be one or more balloons, or other mechanical structure that is expandable into contact with the inner luminal wall of the blood vessel. Desirably, the exit port is forced into contact with the blood vessel wall to shorten the distance that the tissue penetrator projects from the catheter body to the target location. The catheter is particular useful for forming blood flow tracts between blood vessels, in particular in coronary revascularization procedures. Methods of utilizing such a catheter to bypass an arterial obstruction is also disclosed.

18 Claims, 17 Drawing Sheets

U.S. PATENT DOCUMENTS

| | | | |
|---|---|---|---|
| 5,209,749 A * | 5/1993 | Buelna | 606/45 |
| 5,336,176 A * | 8/1994 | Yoon | 604/506 |
| 5,345,940 A * | 9/1994 | Seward et al. | 600/463 |
| 5,366,490 A * | 11/1994 | Edwards et al. | 607/99 |
| 5,464,395 A | 11/1995 | Faxon et al. | |
| 5,588,432 A | 12/1996 | Crowley | 600/439 |
| 5,860,974 A * | 1/1999 | Abele | 606/41 |
| 5,910,150 A | 6/1999 | Saadat | |
| 5,976,107 A | 11/1999 | Mertens et al. | |
| 6,190,353 B1 | 2/2001 | Makower et al. | 604/95 |
| 6,302,875 B1 | 10/2001 | Makower et al. | 604/528 |
| 6,544,230 B1 | 4/2003 | Flaherty et al. | 604/164.2 |
| 6,726,677 B1 * | 4/2004 | Flaherty et al. | 604/528 |

\* cited by examiner

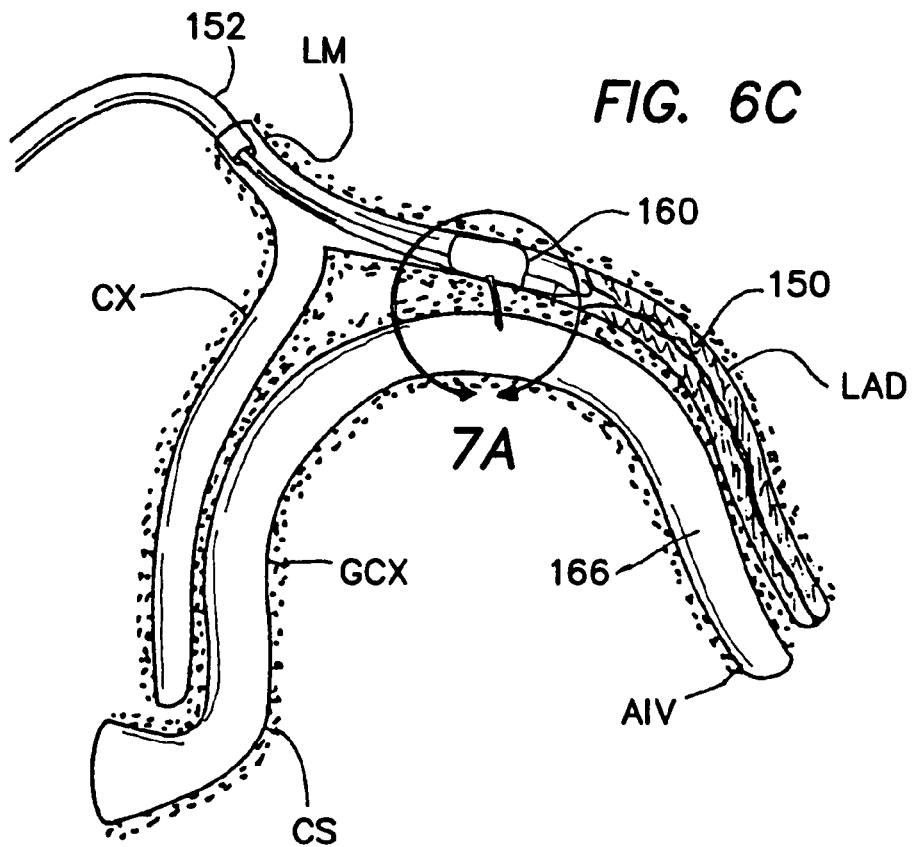
FIG. 6C
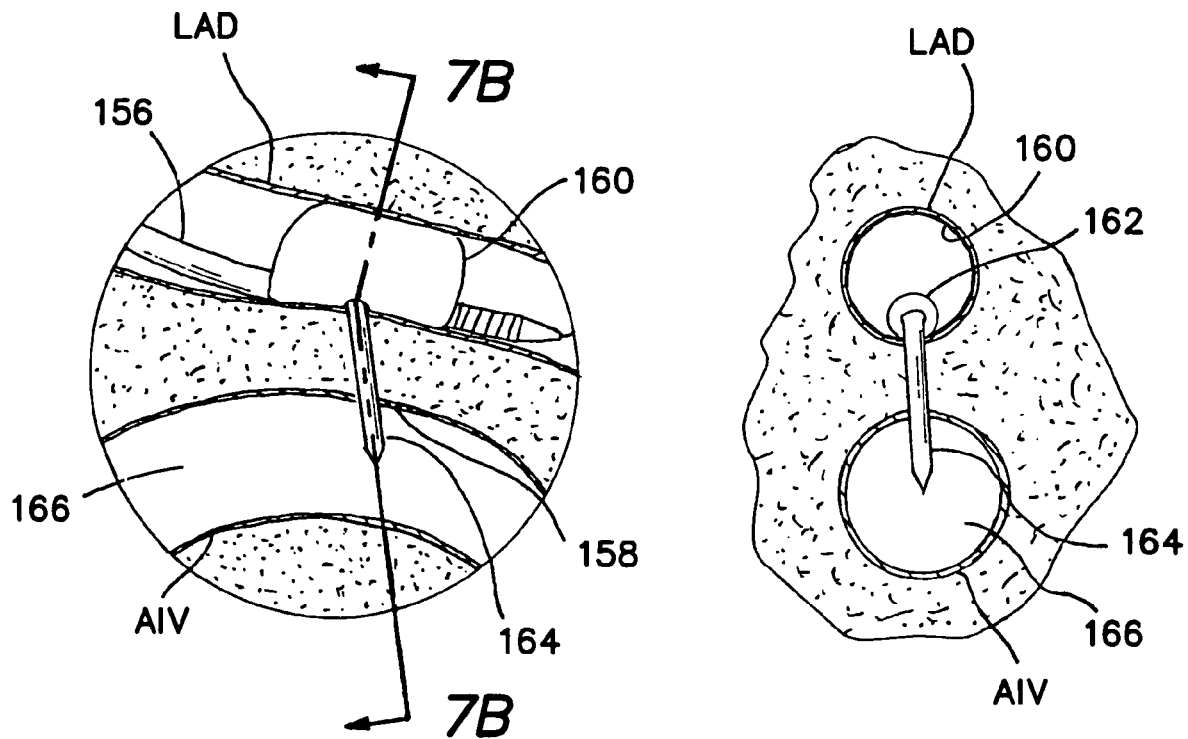
FIG. 7A
FIG. 7B

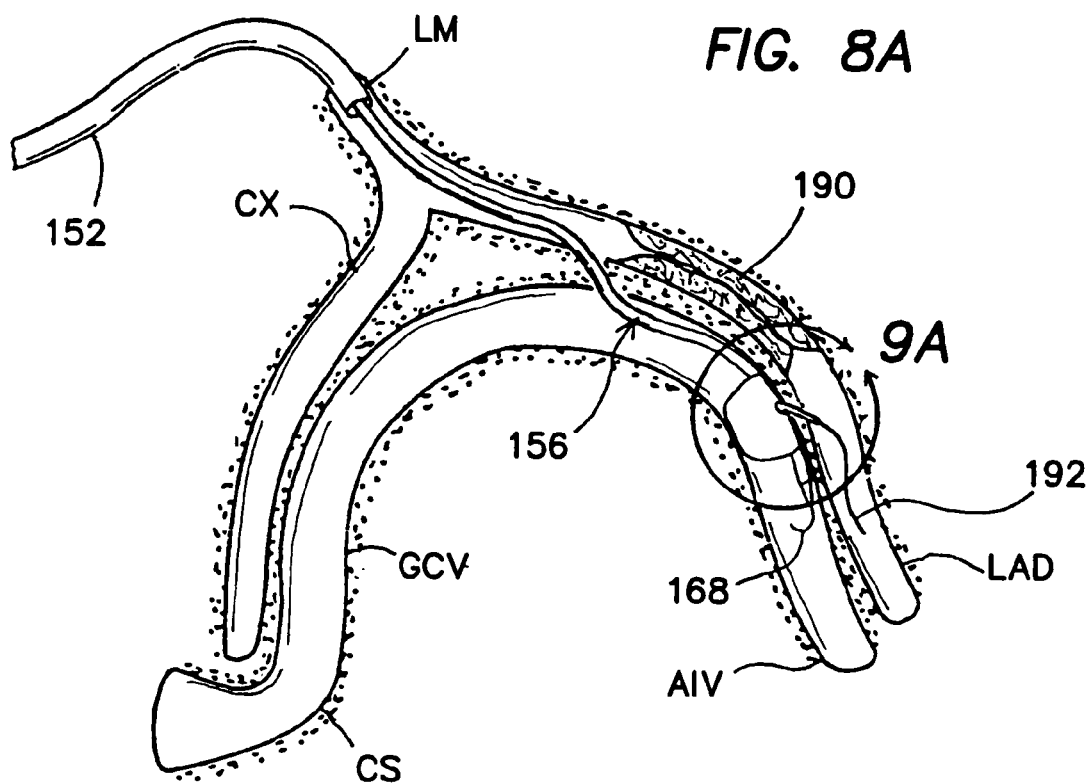
FIG. 8A
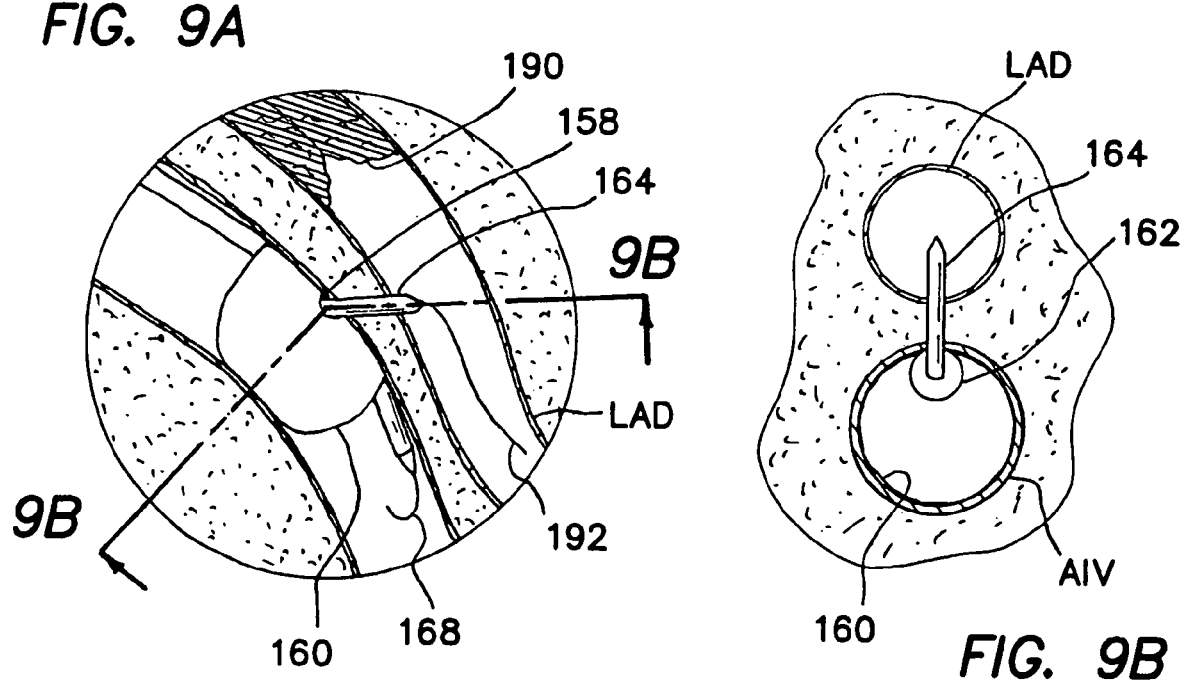
FIG. 9A
FIG. 9B

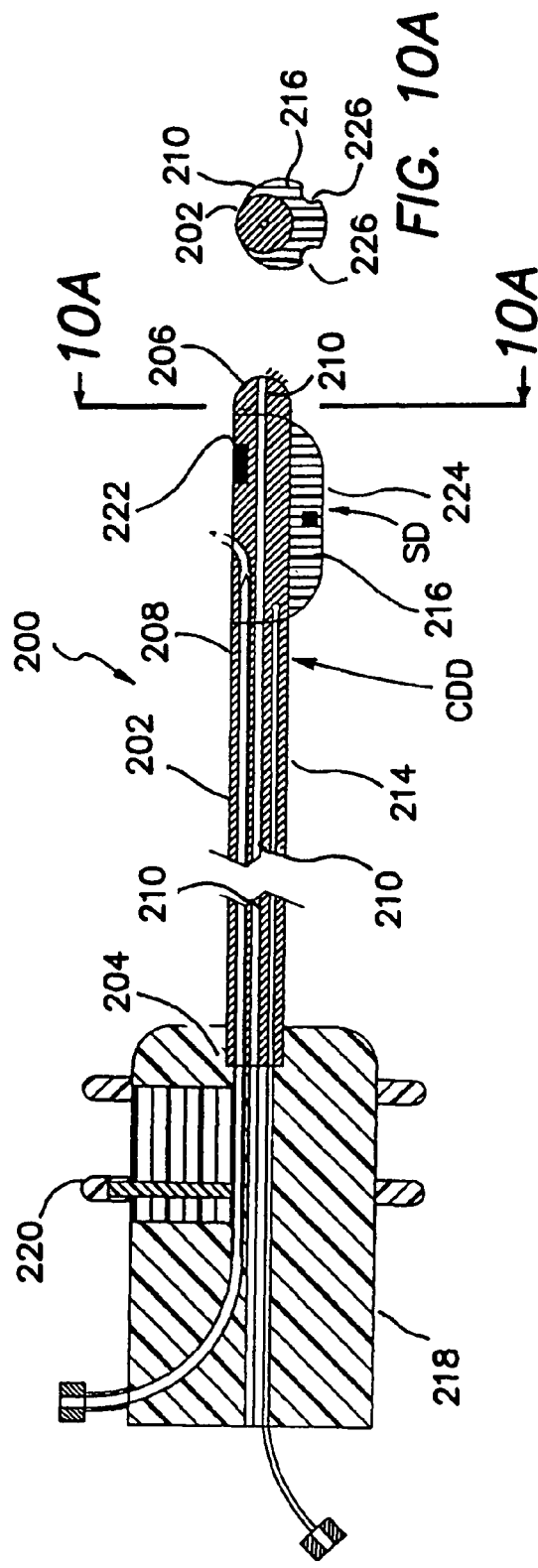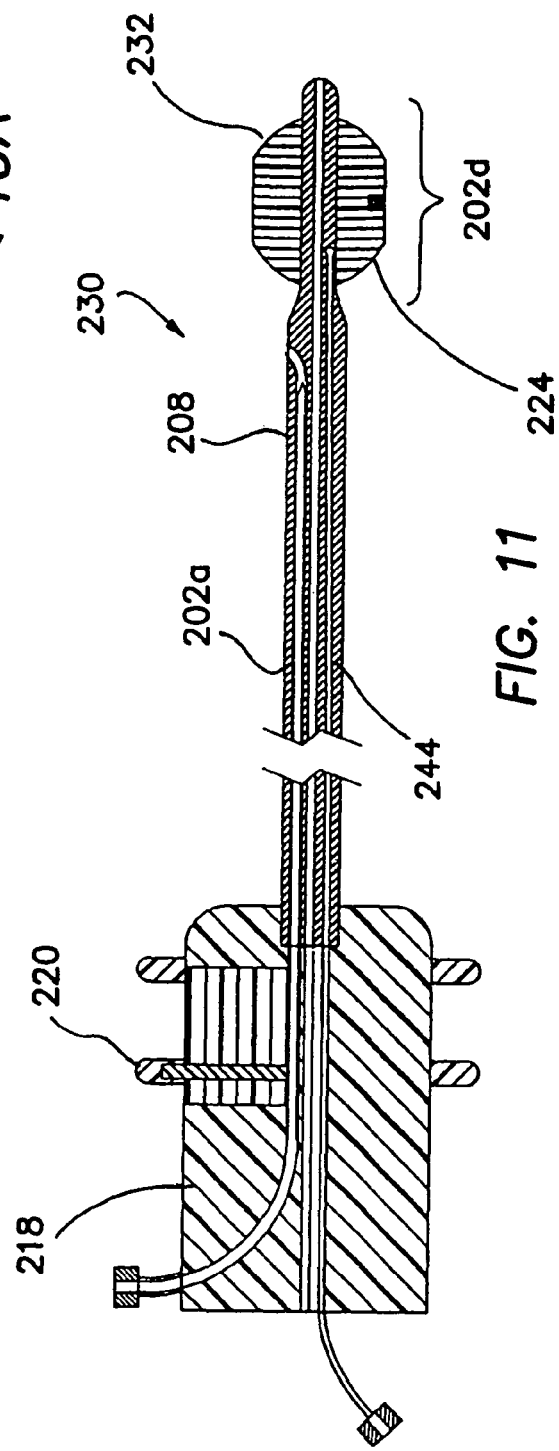

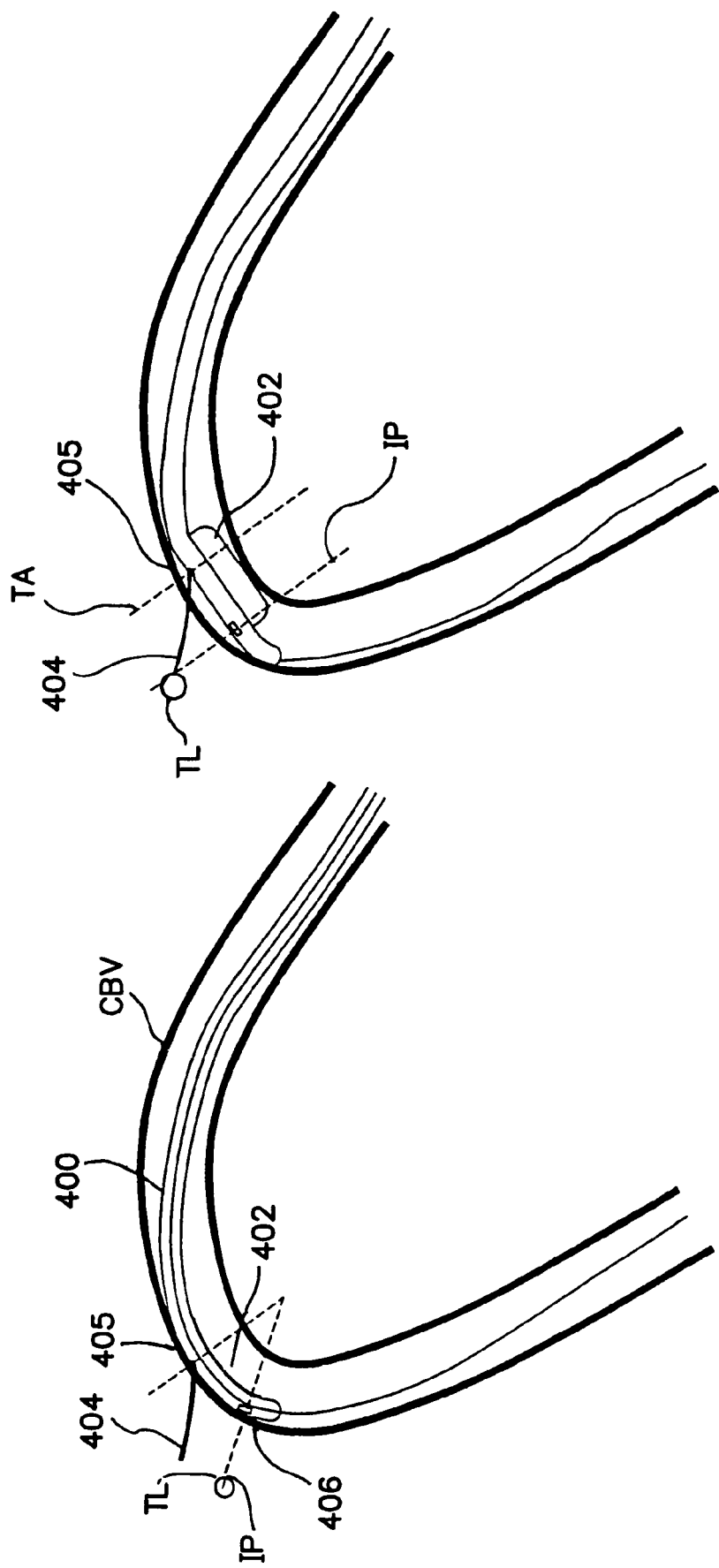

STABILIZED TISSUE PENETRATING CATHETERS

RELATED APPLICATIONS

This application is a continuation-in-part of three-earlier filed and co-pending applications, namely: a) U.S. patent application Ser. No. 09/282,774, filed on Mar. 31, 1999, now U.S. Pat. No. 6,375,615 which in turn claims priority to U.S. Provisional Application No. 60/080,196, filed Mar. 31, 1998; b) U.S. patent application Ser. No. 08/837,294 filed on Apr. 11, 1997 now U.S. Pat. No. 6,302,875, and c) U.S. patent application Ser. No. 09/179,809, filed on Oct. 27, 1998, now U.S. Pat. No. 6,068,638 which is a continuation of U.S. patent application Ser. No. 08/730,496, filed on Oct. 11, 1996, and now U.S. Pat. No. 5,830,222, and which in turn claims priority to earlier-filed U.S. Provisional Patent Application Nos. 60/005,164 filed Oct. 13, 1995 and 60/010,613 filed Feb. 2, 1996, the entire disclosures of all such related applications being expressly incorporated herein by reference.

FIELD OF THE INVENTION

The present invention relates generally to medical devices and methods, and more particularly to catheter devices and methods that are useable to form channels (e.g., penetration tracts) between vessels such as arteries and veins and vessels and other anatomical structures, in furtherance of a therapeutic purpose such as bypassing an arterial blockage, delivering therapeutic agents, creating an A-V dialysis fistula or performing other interventional procedures.

BACKGROUND OF THE INVENTION

Atherosclerotic cardiovascular disease remains a major cause of premature death and morbidity, in most regions of the world. Various transluminal, catheter-based interventional techniques have been used, or proposed for use, to dilate or otherwise treat atherosclerotic obstructions that occur in coronary and/or peripheral arteries. These therapies have traditionally focused on treating the disease intraluminally, or from "within" the vessel lumen.

The devices, systems and methods proposed in previous disclosures from which the present application claims priority introduce a new method of percutaneous revascularization wherein the cardiac veins may either be arterialized, or may be simply used as bypass grafts. Various percutaneous, transluminal techniques have thus been developed for bypassing obstructions in coronary or peripheral arteries through the use of the adjacent vein(s) as in situ bypass conduit(s); (e.g. using catheters to perform extra luminal procedures outside the diseased vessel lumen. In some instances, these procedures may be performed by a venous approach wherein a tissue penetrating catheter is inserted into a vein and the desired passageway or puncture is initially formed by facilitating the passage of a tissue penetrator (e.g., a flow of energy or an elongate penetration member) from a catheter, through the wall of the vein in which the catheter is positioned, and into a target location such as the lumen of an adjacent vessel (e.g. the artery). Alternatively, some of these procedures may be performed by an arterial approach wherein the catheter is inserted into an artery and the desired passageway or puncture is initially formed by facilitating the passage of a tissue penetrator (e.g., a flow of energy or elongate penetration member) from the catheter, through the wall of the artery in which the catheter is positioned, and into the target location such as the lumen of an adjacent vessel (e.g. a vein).

The present invention derives from and expands upon the previous disclosures with respect to stabilizing a tissue penetration catheter in a body lumen.

The prior art has included tissue penetrating catheters for uses other than those claimed in this patent application, but such prior art tissue penetrating catheters fail to include all of the elements required for optimal use in the methods of this invention or for precise targeting of the location at which the penetration tract is to be made. For example, U.S. Pat. No. 5,464,395 (Faxon et al.) discloses a catheter for delivering therapeutic and/or diagnostic agents to tissues surrounding a body passageway (e.g., the lumen of a blood vessel). The catheter devices disclosed by Faxon et al. generally comprise a catheter, a needle cannula that is able to be projected outboard of the catheter so as to deliver the desired agents to the tissue, and preferably one or more inflatable balloons useable to perform a balloon angioplasty procedure in addition to the injection of drugs or other therapeutic or diagnostic agents into tissues surrounding the vessel in which the catheter is positioned. However, the Faxon et al. device does not incorporate any means for precisely aiming its needle to a specific target location. Thus, while the Faxon et al. device may be useable to deliver drugs or other materials to relatively non-specific locations surrounding a vessel in which the catheter is positioned, its lack of sophisticated orientation and aiming apparatus renders it less than optimal for performing injections into specific or discrete target locations such as small anatomical structures, other blood vessels, etc.

Accordingly, there remains a need in the art for the development of new stabilized tissue penetrating catheters that can be used for revascularization, drug delivery, transluminal interstitial interventions and other procedures wherein it is desired to pass a tissue penetrator from a catheter, through the wall of a vessel (e.g, blood vessel or other body lumen) in which the catheter is positioned and to a target location (e.g., another blood vessel, a specific location within tissue, an organ, tumor or other anatomical target structure or lesion.

SUMMARY OF THE INVENTION

The tissue-penetrating catheter must be placed in proper rotational orientation within the blood vessel, prior to facilitating the passage of the tissue penetrator therefrom, to ensure that the tissue penetrator is aimed or positioned to enter the target. To facilitate such aiming of the tissue penetrator, some of the previously described tissue penetrating catheters have included a penetrator direction marker that indicates the direction in which the tissue penetrator will pass from the catheter and an imaging element (e.g., an intravascular ultrasound imaging transducer) that is useable to image the target and the penetrator direction marker. The catheter can then be rotated within the blood vessel until the penetrator direction marker is aligned with the target, thereby indicating that subsequent advancement of the tissue penetrator from the catheter will result in the formation of the desired penetration tract between the blood vessel in which the catheter is positioned and the target.

The catheter stabilizers of the present invention facilitate accurate and reliable positioning, aiming and actuation of a tissue penetrating catheter in a blood vessel so that an adjacently located blood vessel or other anatomical target can be accurately penetrated. Also, the catheter stabilizers of the present invention may serve to perform other functions as enumerated herebelow.

In accordance with the invention, there are provided tissue penetrating catheter devices that generally comprise a) an elongate catheter body, a tissue penetrator (e.g., solid or hollow needle, knife, blade, radiofrequency cutter, bipolar tissue cutter, monopolar tissue cutter, laser or other flow of tissue-penetrating energy) that is passable or advanceable from the catheter body to penetrate outwardly through the wall of a blood vessel or other tubular anatomical structure in which the catheter is positioned to a target location (e.g., another blood vessel, organ, interstitial location, tumor, etc.) and c) a stabilizer that is deployable laterally in at least one direction from the catheter body prior to and/or during passage or advancement of the penetrator to stabilize (e.g., deter some movement of) at least a portion of the catheter body within the vessel (e.g., blood vessel or other tubular anatomical structure) in which the catheter body is positioned. The stabilizer may comprise any suitable type of moveable or expandable member, such as:

- a compliant balloon;
- a non-compliant balloon;
- an self-expanding frame formed of wire, metal or polymer mesh or other suitable material (e.g., spring steel, elastic, self expanding material, shape memory material such as a NiTi alloy) that transitions from a non-deployed configuration to a deployed configuration in response to a temperature change or passage of energy therethrough, such frame being initially restrained by a sheath, clip or other restraint means and being subsequently expandable to its deployed configuration upon removal of the restraint therefrom;
- a substantially rigid member or foot that is extendable laterally from the catheter body (e.g., in a direction that is radially opposite the direction in which the tissue penetrator passes from the catheter body; or,
- a portion of the catheter body itself that is adapted to curve, loop or otherwise deform when desired to thereby stabilize the position of the catheter body within the vessel.

Still further in accordance with the invention, deployment of the stabilizer may accomplish one or more of the following effects:

- prevention of movement of at least a portion of the catheter body during tissue penetration;
- bringing the tissue penetrating catheter body closer to the target (thereby minimizing the distance that must be traveled by the tissue penetrator;
- blocking blood flow through the vessel (e.g., blood vessel or other anatomical structure) in which the catheter body is positioned;
- providing hemostasis during and/or after the tissue penetration;
- causing tamponade or compression of tissues or structures located adjacent the penetration tract created by the tissue penetrator;
- dilating the vessel (e.g., blood vessel or other anatomical structure) in which the catheter body is positioned to facilitate advancement of the tissue penetrating catheter or for other purposes;
- dilating or opening the vessel (e.g., blood vessel or other anatomical structure) with a balloon or expandable stabilizer/dilator and subsequently using the balloon or expandable stabilizer/dilator to stabilize the catheter while allowing some blood flow past or through the balloon or expandable stabilizer/dilator.
- straightening the catheter body in the area of the tissue penetrator and/or any imaging element to facilitate imaging and/or aiming of the tissue penetrator at the target;

Still further in accordance with invention, the catheter stabilizer may include material that is imageable by radiographic, ultrasound or other means, such stabilizer thereby performing additional functions as a marker to facilitate longitudinal and or rotational positioning of the catheter within the vessel. In this regard, in embodiments wherein the stabilizer comprises an inflatable balloon, the balloon made be inflated with a radiographic contrast medium thereby rendering the balloon radiographically visible. In other embodiments, imageable elements such as a metal wire, foil or other material made be positioned at one or more discrete locations such as at the outer-most extent of the stabilizer when the stabilizer is fully deployed, thereby providing marker(s) that may be used to facilitate precise rotational positioning of the catheter body and aiming of the tissue penetrator at the target.

Still further in accordance with the invention, the stabilizer and/or catheter body may incorporate one or more flow-through channels to permit blood flow to pass the stabilizer when the stabilizer is deployed.

Still further in accordance with the invention, the catheter body may incorporate one or more infusion lumens with infusion ports to permit dye or other imageable material to be injected upstream of the deployed stabilizer to check for flow-through or past the stabilizer or alternatively occlusion of the vessel, in situations where it is desired for the stabilizer to effect such occlusion. In this regard, it will be noted that in some applications it may be desirable for the stabilizer to be deployed such that it expands substantially across the luminal diameter of the vessel but does not firmly coapt with the vessel wall. In such embodiments, the ability to inject radiographic contrast medium, dye or other material upstream of the stabilizer will enable the operator to determine the amount of blood flow that is being permitted to pass the stabilizer, thereby ascertaining whether the stabilizer has been deployed or extended to its desired position or whether more or less deployment or extension is necessary prior to proceeding with the procedure.

The invention together with additional features and advantages thereof may best be understood by reference to the following description taken in connection with the accompanying illustrated drawings.

BRIEF DESCRIPTION OF THE DRAWINGS

FIGS. 6A-6I illustrate the triangle of Brock-Moscheau (a name given to the formation bounded by the relationship between certain arteries and veins of the heart) and show byway of example a preferred method that can be carried out in accordance with the teachings of this invention.

FIG. 7A is an enlarged view of the circle 7A of FIG. 6C.

FIG. 7B is a transverse sectional view taken along line 7B-7B of FIG. 7A.

FIGS. 8A-8C illustrate the triangle of Brock-Moscheau (a name given to the formation bounded by the relationship between certain arteries and veins of the heart) and show by way of example another preferred method that can be carried out in accordance with the teachings of this invention.

FIG. 9A is an enlarged view of the circle 9A of FIG. 8A.

FIG. 9B is a transverse sectional view taken along line 9B-9B of FIG. 9A.

FIG. 10 is a longitudinal sectional view of an embodiment of a tissue penetrating catheter having a non-concentric, balloon-type stabilizer wherein flow-through channels are formed to permit blood flow past the stabilizer when the stabilizer is fully deployed.

FIG. 10a is a cross-sectional view through line 10a-10a of FIG. 10.

FIG. 11 is a longitudinal sectional view of an embodiment of a tissue penetrating catheter having a tapered distal portion whereon a balloon is formed, such balloon being usable for both a) stabilizing the catheter body and b) dilating an obstruction or narrowing of the vessel to facilitate advancement of the catheter body to the desired location.

FIG. 15a is a schematic view of a stabilized tissue penetrating catheter of the present invention which has been inserted into a curved blood vessel and wherein the stabilizer of the catheter is yet to be deployed.

FIG. 15b is the same view as FIG. 15a, but wherein the stabilizer member of the catheter has been deployed and performs a dual function of a) stabilizing the catheter within the blood vessel and b) straightening the portion of the catheter from which the tissue penetrator extends to thereby improve the imageability of the target and the aiming of the tissue penetrator.

DETAILED DESCRIPTION OF THE PREFERRED EMBODIMENTS

Set forth herebelow are detailed descriptions of certain embodiments and examples of the catheter devices and methods of the present invention.

The invention herein utilizes the vascular system as a perfect conduit to any region of the body. The devices, systems and methods described herein provide a new way that the interstitial space can be accessed for surgical, interventional, diagnostic, monitoring or other purposes. The invention provides a system for gaining percutaneous access to any part of the body through the vascular system, and provides the basic set of instrumentation for accomplishing several surgical and medical end-points.

The stabilized tissue penetrating catheters of the present invention are usable in the performance of certain transluminal catheter-based revascularization procedures such as the PICAB™ and PICVA™ procedures in the heart or peripheral blood vessels as described in Fitzgerald, P. J, *New Approaches and Conduits: In Situ Venous Arterialization and Coronary Artery Bypass*, 1 CURRENT INTERVENTIONAL CARDIOLOGY REPORTS 127 (1999). Additionally, the stabilized tissue penetrating catheters of the present invention are useable in a wide range of other procedures as described in U.S. Pat. No. 5,830,222 (Makower) and U.S. patent application Ser. No. 09/505,149, filed Feb. 15, 2000, entitled Sterility Barriers for Insertion of Non-Sterile Apparatus Into Catheters or Other Medical Devices and in published PCT Applications WO 98/16161, WO 98/46119, WO 99/49910 and WO 99/49793, the entire disclosures of which are expressly incorporated herein by reference. Examples of the other types of procedures in which these tissue penetrating catheters may be used include but are not limited to delivery of drugs or other substances to desired locations within the body, creating arterio-venous fistulas for renal dialysis or other purposes, performing transjugular intrahepatic portosystemic shunt procedures (TIPS Procedures) for the treatment of liver cirrhosis and portal hypertension or performing other transluminal, or performing other catheter based procedures wherein the vascular system or other anatomical passageways of the body are used as may be used as conduits to access a desired location outside of the vascular system or other anatomical passageway through which the catheter has been advanced, such as, the insertion of various instrumentation to effect a surgical effect, gaining transvascular intracranial access and subsequent therapeutic or diagnostic intervention to various perivascular tumors, hemorrhages, stroke-effected areas and diseased zones; transvascular tissue biopsies from the brain, heart, kidney, liver, lung or bone; transvascular implantation or instillation of drugs, materials or devices such as sensors, radioactive seeds, ferromagnetic particles, balloons, cells or genetic material.

Figure 1:
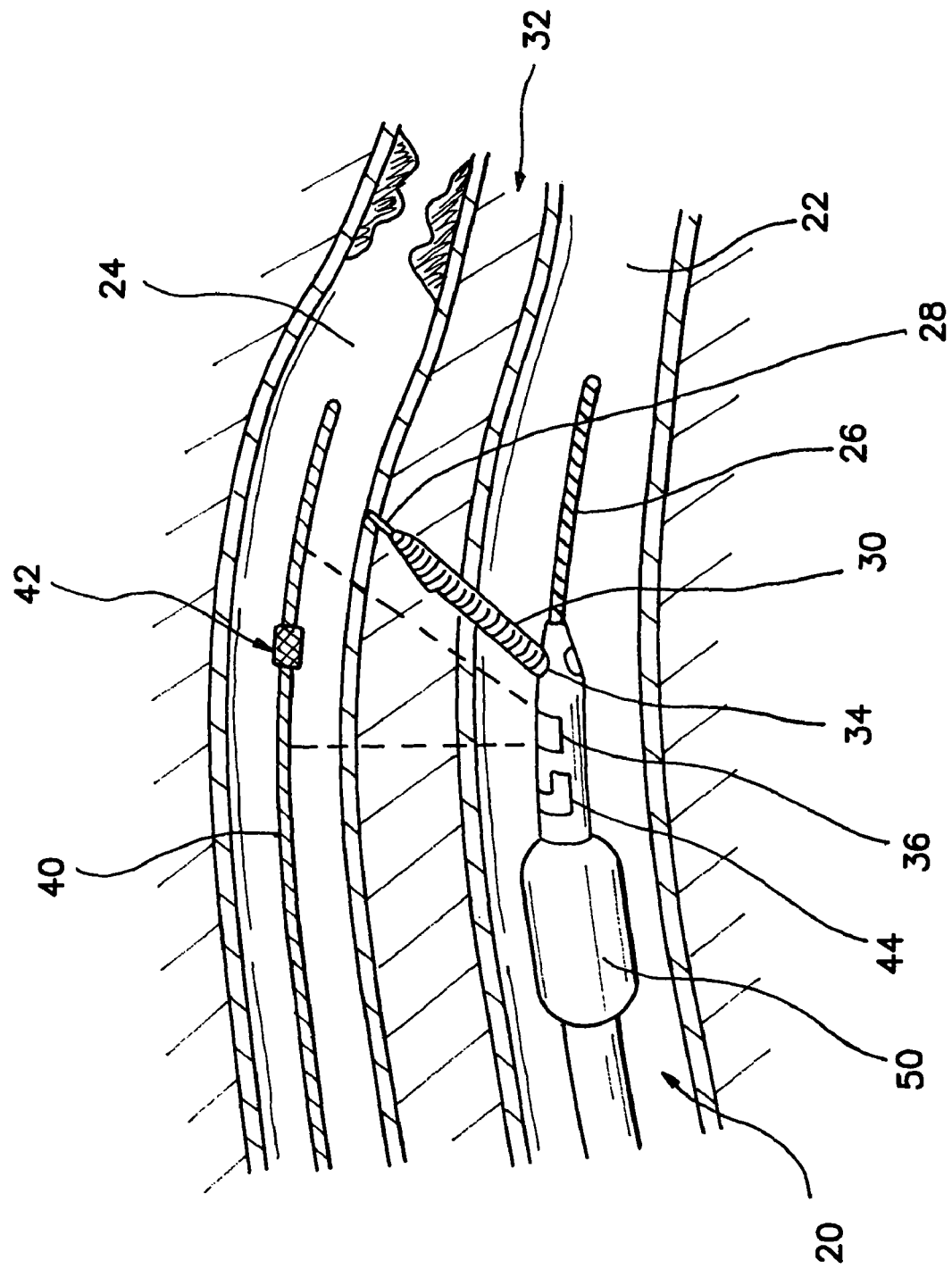
FIG. 1 is a sectional view through adjacent blood vessels, showing a penetration catheter of the present invention located in one of the blood vessels directing a penetrating element through intervening tissue to the other blood vessel, in conjunction with a receiver/transmitter on a guidewire in the other vessel.

Examples of Balloon-Stabilized Penetration Catheters:

FIG. 1 illustrates a transvascular interstitial surgery (TVIS) catheter 20 (or "tissue penetrating catheter") located within a first blood vessel 22 that extends generally parallel to a second blood vessel 24; the second blood vessel more generally symbolizing an adjacent body cavity. The catheter 20 includes a central lumen (not shown) for advancing the catheter over a guidewire 26. A tissue penetrating element, which may comprise a probe 28 advanced within a sheath 30, is shown deployed generally transversely with respect to the longitudinal axis of the catheter 20 through the wall of the first blood vessel 22, through intervening tissue 32, and through the wall of the second blood vessel 24. Typically, the tissue penetrating element translates through a longitudinal lumen in the catheter 20 and is deflected at a distal tip of the catheter to exit transversely through a side opening 34.

Various means are known for penetrating tissue, wherein the probe 28 and sheath 30 may or may not be advanced simultaneously, and may have the following configurations: the sheath 30 may be a sharp-tipped or semi-rigid cannula capable of being inserted into the tissue alone; the probe 28 may be a relatively rigid wire, antenna, light guide or energy guide capable of being inserted into the tissue alone or with the support of the sheath 30; or further the probe 28 and sheath 30 may be operatively linked where the two are inserted together into the tissue. In this manner, an access port or channel may be formed between the two blood vessels 22, 24. Once the sheath 30 is placed, a more floppy guidewire can be placed through it to permit the advancement of additional instrumentation into the second blood vessel 24. Alternatively, no guidewire may be necessary if the interstitial space 32 is being entered to perform a different type of procedure.

To facilitate positioning, orientation, and aiming of the tissue penetrating element, the catheter 20 may also be provided with an active orientation detecting device 36, such as, for example, an ultrasound transducer. The active orientation detecting device 36 may be a simple piezo-electric, wire or silicon based slab capable of sending and receiving a signal to detect the presence or velocity of flow within an adjacent vessel; or this same device could be an array of receivers in relationship to a transmitter for the purposes of providing an image of the surrounding tissue.

A secondary guidewire 40 may be advanced through the second blood vessel 24 to help in positioning and orienting the TVIS catheter 20. In particular, a receiver/transmitter 42 may be provided on the secondary guidewire 40 to work in conjunction with the active orientation detecting device 36. In this regard, the active orientation detecting device 36 could be a simple transmitter capable of sending a signal to guidewire receiver/transmitter 42, which in turn returns a signal to the operator upon detection of the signal emitted by the active orientation detecting device 36. Conversely, the receiver/transmitter 42 may send a signal to the active orientation detecting device 36.

Additionally, a passive orientation device 44 may be provided on the TVIS catheter 20 to allow for radiographic, fluoroscopic, magnetic, or sonographic detection of the distal portion of the catheter 20 within the body. These materials include but are not limited to any radiopaque material such as barium or steel, any ferromagnetic material such as those with iron, or any material or composite which provides sufficient interference to sound waves such as trapped air bubbles, scored metal or several laminates.

In accordance with the present invention, an inflatable stabilizing balloon 50 is provided on the TVIS catheter 20 near the side opening 34. The balloon 50 functions to block blood flow through the first blood vessel 22, stabilize the catheter 20 within the vessel, or dilate the vessel.

In a particular embodiment shown in FIG. 1, the balloon 50 is located sufficiently close to the side opening 34 so as to maintain the radial position of the side opening 34 when deploying the tissue penetrating element therefrom. That is, deploying the tissue penetrating element through the wall of the vessel 22, intervening tissue 32, and wall of the second vessel 24, results in a certain amount of reaction force to the distal tip of the catheter 20. The balloon 50 expands into contact with the wall of the blood vessel 22 opposite from the direction of deployment of the tissue penetrating element, and thus provides rigidity to the otherwise flexible catheter in the area of the side opening 34. As a consequence, the catheter at the side opening 34 remains in place and the tissue penetrating element more easily passes through the intervening tissue into the second blood vessel 24. To insure stabilization of the catheter at the side opening 34, the balloon 50 may be positioned immediately adjacent or close to that side opening 34. Additionally, the size, shape and position of the balloon may vary, depending on the other functions that are intended to be performed by the balloon 50. For example, in embodiments where it is desired for the balloon to create hemostasis or fully occlude blood flow through the vessel, the balloon may be formed concentrically about the catheter body and sized so than when it is inflated it will firmly coapt with the wall of the blood vessel thereby blocking blood flow past the balloon 50. In other embodiments, where it may be desired for the balloon to compress or tamponade tissue adjacent the penetration tract created by the advancement of the tissue penetrating element, the balloon may be located around or on either side of the outlet of the tissue penetrating element such that it will exert pressure against the desired tissue during or immediately after advancement of the penetrator element. Similarly, in some embodiments, the balloon 50 may be configured to stretch or draw taut the wall of the blood vessel to facilitate the ease by which the penetrator passes through the blood vessel wall and to prevent out-pouching or "tenting" of the blood vessel wall during penetration.

Figure 3:
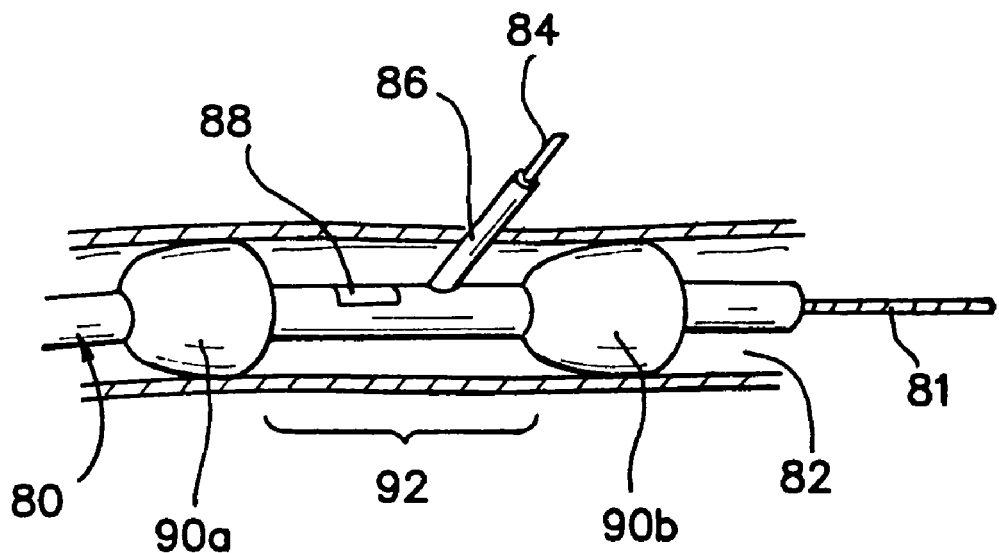
FIG. 3 is a sectional view through a blood vessel showing a penetration catheter on the present invention with a pair of balloons for stabilizing a span of the catheter therebetween from which a tissue penetrating element extends.

FIG. 3 illustrates still another TVIS catheter 80 in accordance with the present invention. The catheter 80 is adapted to advance over a guidewire 81 through a blood vessel 82 and transversely deploy a tissue penetrating element, such as a probe 84 within a sheath 86. Again, the tissue penetrating element is designed to pass through the wall of the blood vessel 82, through any intervening tissue, and into an adjacent body cavity. In this regard, the catheter 80 may be positioned and aimed using an active orientation detection device 88.

The catheter 80 is also provided with a pair of balloons 90*a*, 90*b* disposed on both sides of the tissue penetrating element. More specifically, a proximal balloon 90*a* and a distal balloon 90*b* define a span 92 of the catheter 80 therebetween from which the tissue penetrating element is deployed. Because both of the balloons 90*a*, 90*b* contact the wall of the blood vessel 82 opposite from the direction that the tissue penetrating element extends, the span 92 is maintained generally centrally within the blood vessel. That is, the span 92 is sufficiently short so that there is minimal deflection thereof from the reaction forces imparted when advancing the tissue penetrating element from the catheter 80 and into surrounding tissue. In a preferred embodiment, the spacing of the two balloons 90*a*, 90*b* is such that the span 92 is less than about 30 mm.

Figure 4A:
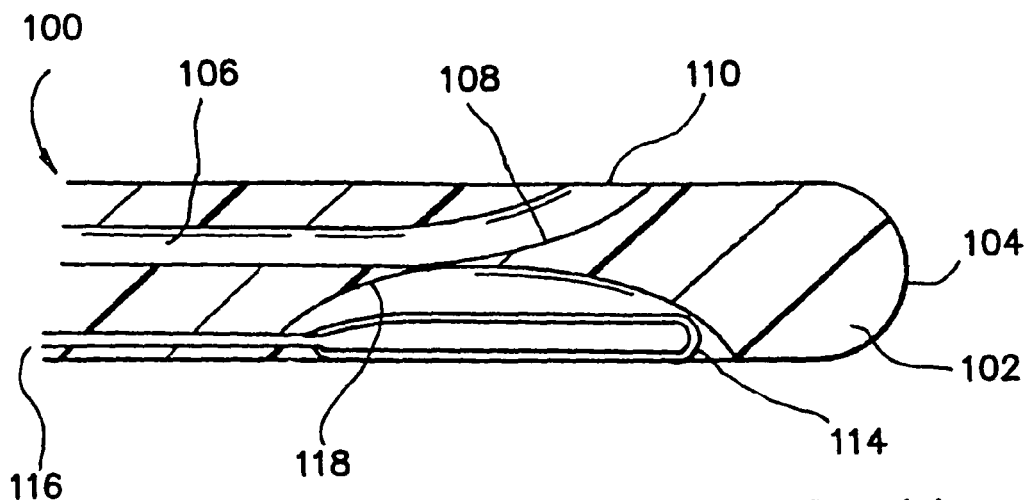
FIG. 4A is a longitudinal sectional view through a tissue penetration catheter of the present invention having an inflatable balloon mounted thereon for stabilizing the portion of the catheter from which a tissue penetrating element extends, the balloon shown deflated.

FIG. 4A illustrates a further embodiment of a tissue penetration catheter 100 of the present invention having means for stabilizing a portion thereof from which a tissue penetrating element will project. Specifically, the catheter 100 includes a catheter body 102 terminating at a distal tip 104. A working lumen 106 extends longitudinally through the catheter body 102, preferably into proximity with the distal tip 104. The working lumen 106 is sized to receive a tissue penetrating element (not illustrated) suitable for passing through body tissue and desirably forming a channel therethrough. The lumen 106 includes a curved deflecting portion 108 and terminates in a side opening 110. The tissue penetrating element is flexible and is deflected by curved portion 108 to project transversely from the catheter 100. Although not shown, the catheter 100 may also be provided with means for positioning and orienting the side opening 110 so that the tissue penetrating element passed through lumen 108 will be aimed toward a particular anatomical structure external to the blood vessel in which the catheter 100 is positioned.

An inflation balloon 114 attaches to the catheter body 102 in the region of the side opening 110 and is supplied with a suitable inflation fluid or gas via an inflation lumen 116. In the illustrated embodiment, the balloon 114 is positioned within a smoothly curved recess 118 so as not to project radially outwardly from the generally cylindrical catheter body 102. In other embodiments, the balloon may be provided on the exterior of the cylindrical catheter body 102, without such a recess 118.

Figure 4B:
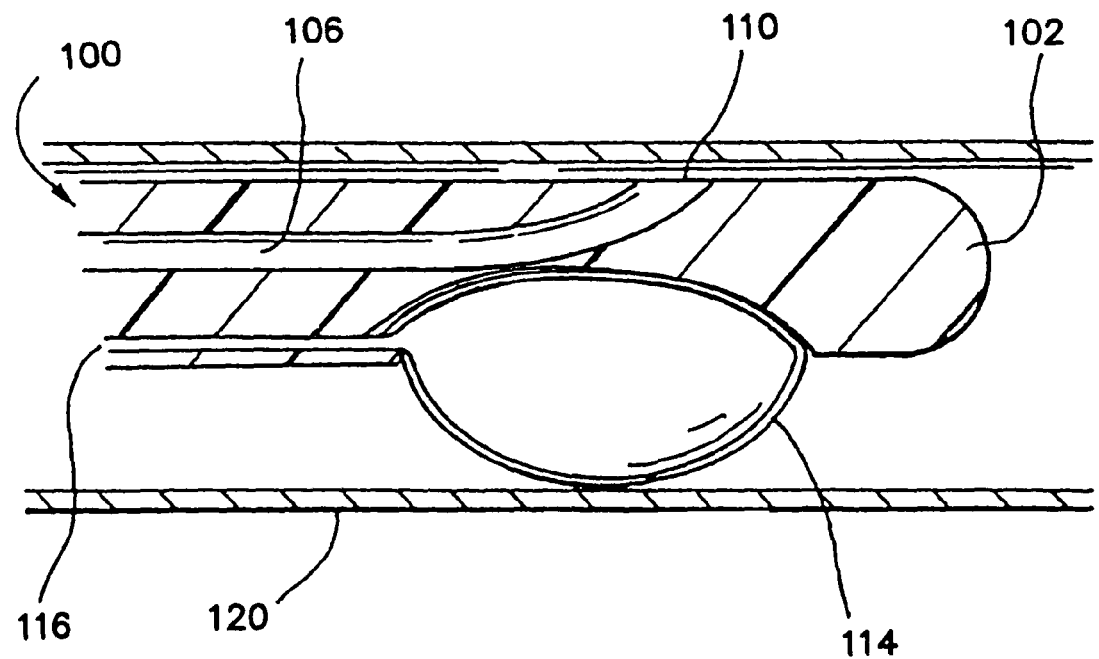
FIG. 4B is a longitudinal sectional view through the catheter of FIG. 4A positioned within a blood vessel with the stabilizing balloon shown inflated to contact a wall of the vessel opposite the direction that the tissue penetrating element will project.

The catheter 100 is shown in FIG. 4B positioned within a blood vessel 120 with the balloon 114 inflated. Inflation of the balloon 114 forces the catheter body 102 against one wall of the blood vessel 120; in this case, the catheter body is forced upward. In the preferred embodiment, the balloon 114 is positioned on the catheter body 102 with respect to the side opening 110 so as to press the side opening against the wall of the blood vessel. Because the balloon 114 is maintained in its inflated state, it provides a portion of catheter 100 in contact with the wall of blood vessel opposite from the direction that the tissue penetrating element will project. That is, the tissue penetrating element extends through lumen 106 and transversely out the opening 110, immediately passing through the wall of the blood vessel 120 because the balloon 114 holds the opening against the blood vessel wall. Because of the stabilization and reaction force provided by the balloon 114, the tissue penetrating element more easily passes through the vessel wall and into adjacent tissue and/or body cavity. Also, the balloon 114 shown in this embodiment is positioned on the catheter at a location where it will prevent or deter torquing of the catheter during the advancement of the tissue penetrating member or probe from lumen 106 and out of opening 110.

Figure 5A:
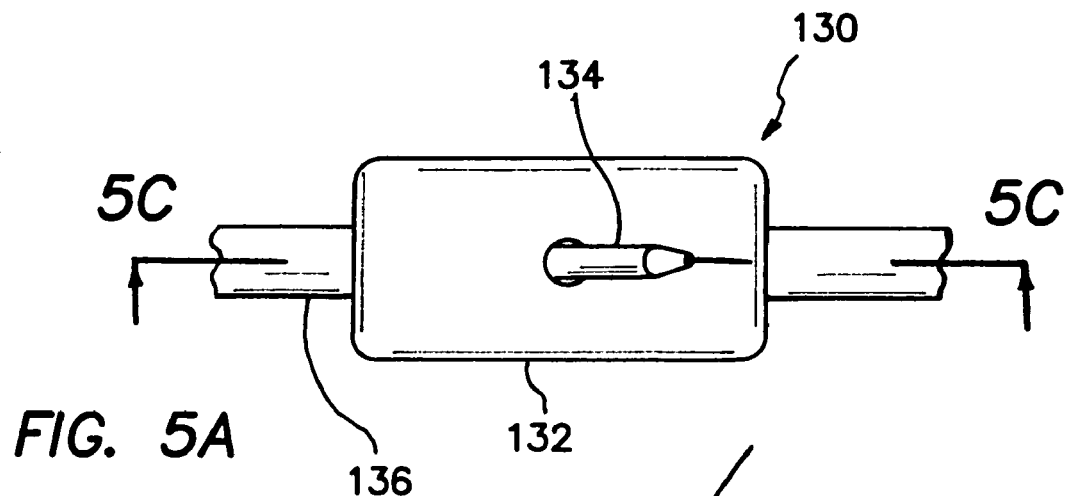
FIG. 5A is a top plan view of an alternative tissue penetrating catheter of the present invention having a concentric balloon stabilizer.
Figure 5B:
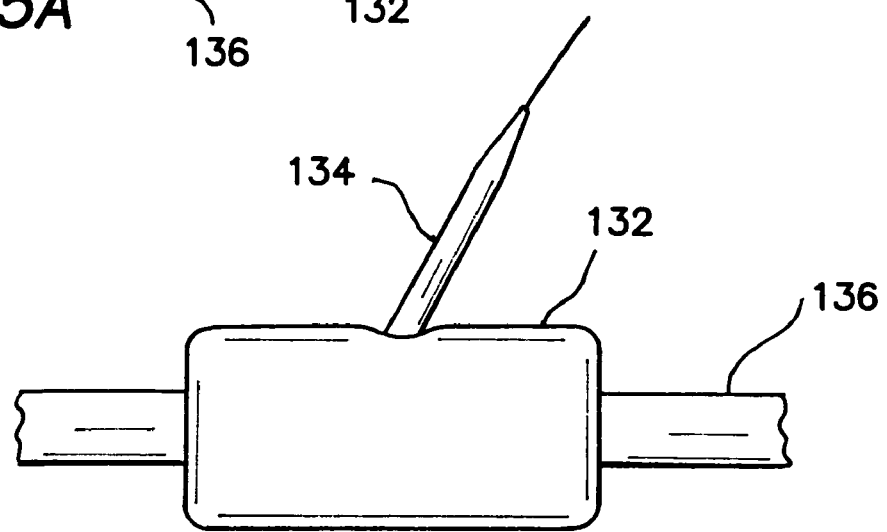
FIG. 5B is a side elevational view of the tissue penetrating catheter of FIG. 5A.
Figure 5C:
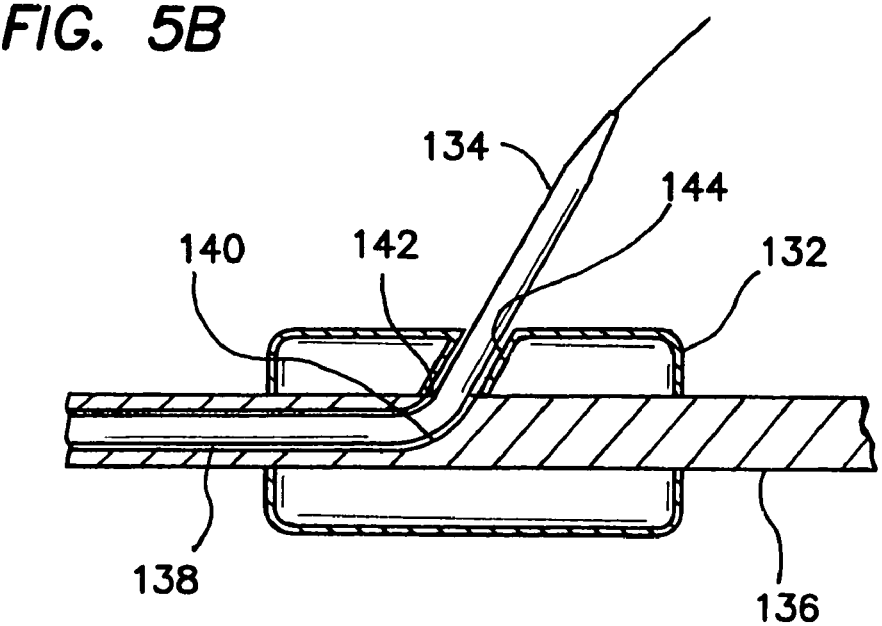
FIG. 5C is a longitudinal sectional view taken along line 5C-5C of FIG. 5A.

FIGS. 5A-5C illustrate a further embodiment of the tissue penetrating catheter 130 having a stabilizing balloon 132 concentrically mounted thereon through which a tissue penetrating element 134 transversely projects. The catheter 130 includes an elongate flexible catheter body 136 having a lumen 138 through which the tissue penetrating element 134 translates. The lumen 138 includes a curved deflecting portion 140 that causes the tissue penetrating element 134 to deflect transversely through a side opening 142 in the catheter body 136.

The balloon 132 is mounted so as to surround the side opening 142 and includes a through bore 144 aligned with the opening to accommodate passage of the tissue penetrating element 134. In the illustrated embodiment, the through bore 144 is angled slightly distally to accommodate the exit angle of the tissue penetrating element 134 from the lumen 138. In other embodiments, the tissue penetrating element 134 may project perpendicular to the catheter body 136, or may even be angled in a proximal direction. The through bore 144 will be angled accordingly so as to prevent puncture of the balloon by the tissue penetrating element 134.

In use, the balloon 132 is deflated, and tissue penetrating element 134 resides fully within the lumen 138. The catheter 130 is advanced through the vasculature of the patient to a desired location within a host blood vessel. In this regard, location and orienting means as described above may be provided on the catheter 130. Once in position, and with the side opening 142 aimed toward the target location external to the host blood vessel, the balloon 132 is inflated.

As described above, inflation of the balloon 132 stabilizes the catheter 130, and facilitates operation of the tissue penetrating element 134. That is, the balloon 132 contacts the wall of blood vessel, and fills the lumen therein. The outer opening of the through bore 144 is thus pressed against the inner wall of blood vessel, and advancement of the tissue penetrating element 134 causes it to immediately pierce the wall of the blood vessel. Because the balloon 132 contacts the opposite blood vessel wall, any reaction forces imparted by the surrounding tissue to the tissue penetrating element 134, as transmitted to the catheter 130, will be resisted. That is, the catheter body 136 will be stabilized in its central location within the blood vessel.

An Example of a PICVA Procedure Using a Stabilized Penetration Catheter:

A Percutaneous In Situ Coronary Venous Arterialization (PICVA) procedure is useable to effectively provide arterial perfusion of an ischemic region of myocardium, even in cases where a coronary artery is so extensively obstructed that no patent distal portion of the artery remains available to carry bypassed arterial flow.

Figure 6A:
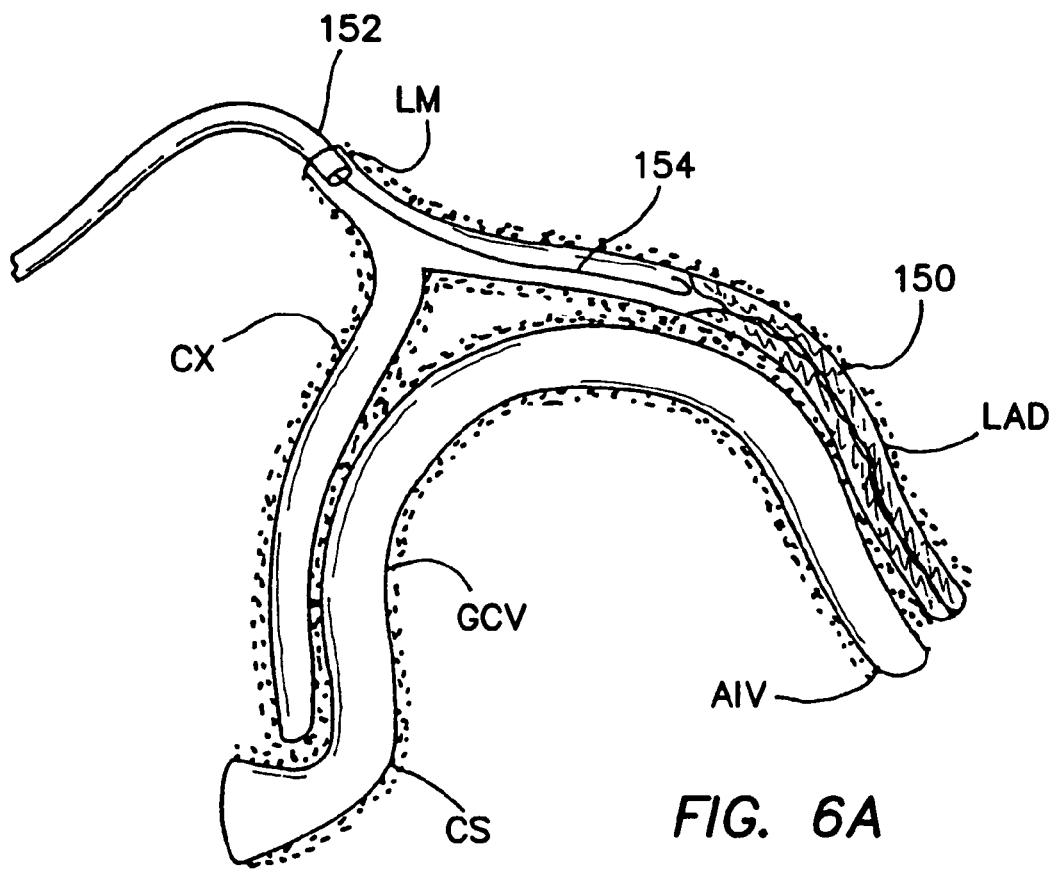

FIG. 6A is a diagram of a portion of the coronary vasculature known as known as the Triangle of Brock-Moscheau. The Triangle of Brock-Moscheau is defined by the left anterior descending coronary artery LAD, the circumflex coronary artery CX, and the anterior inter ventricular vein AIV. The arteries CX and LAD are both joined to and receive blood from the left main artery. The great coronary vein GCV forms a downwardly opening U-shaped configuration with the legs of the U being adjacent to arteries CX and LAD. Obstructions resulting from a build up of plaque may be found in either or both of the arteries CX and LAD. For example and for purposes of illustrating a preferred embodiment of the method of this invention, FIG. 6A shows an obstruction 150 in the left anterior descending artery LAD.

In the first step of the procedure, a coronary guide catheter 152 is advanced into the left coronary ostium and a guidewire 154 such as a 0.014 inch guidewire is advanced through the guide catheter 152 into the lumen of the left anterior descending artery (LAD) to a location just proximal of the obstruction 150.

Figure 6B:
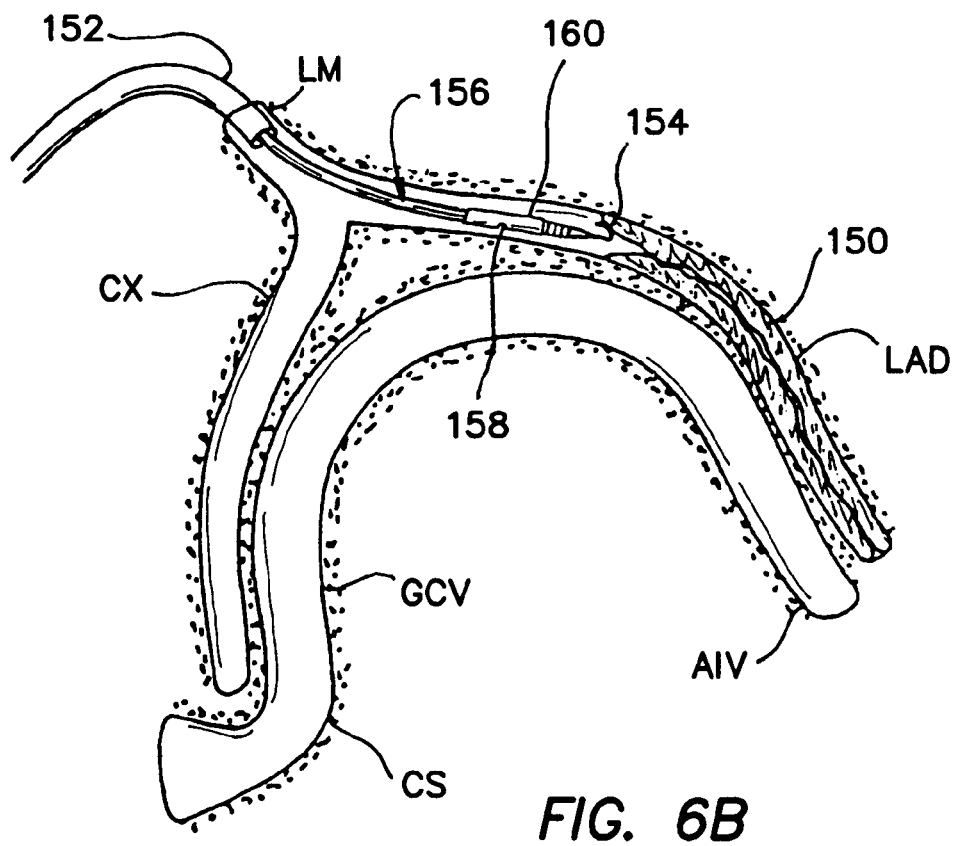

Next, as shown in FIG. 6B, a tissue penetrating catheter 156 of the present invention is percutaneously inserted and transluminally advanced through the guide catheter 152 and over the guidewire 154 into the left anterior descending artery LAD to a location just proximal of the obstruction 150. The axial position of the guidewire 154 and of the catheter 156 within the artery LAD is known by conventional techniques which may include, for example, fluoroscopy and a radiopaque marker on the catheter 156. With the catheter 156 in position within the LAD, an imaging transducer on the catheter may be actuated to obtain images of anatomical structures adjacent to the LAD, such as the anterior inter ventricular vein AIV. The catheter 156 is moved, and more specifically rotated within the artery LAD until an exit port 158 and hence a penetrator path is aimed at the lumen of the vein AIV. FIG. 6B also shows a balloon 160 at the location of the exit port 158 in a deflated state.

At this point, as shown in FIGS. 6C and 7A, the catheter 156 is stabilized within the LAD at the location of the exit port 158 using any of the means described herein. As illustrated, the balloon 160 attached to the catheter 156 is inflated so as to press the exit opening 158 against the wall of the LAD closest to the target structure; in this case, the adjacent vein AIV.

FIG. 7B illustrates a preferred embodiment of the catheter 156 configuration in which the balloon 160 is attached to a body 162 of the catheter 156 in a manner that causes the body 162 to be offset from the center of the balloon when inflated. Consequently, the exit port 158 is located closely adjacent to or in contact with the wall of the artery LAD when the balloon 160 expands. This is in contrast to the earlier-described embodiment of FIGS. 5A-5C in which the balloon is concentrically expanded around the catheter body. The non-concentric balloon 160 may extend axially on both sides of the exit port 158, or may be axially offset from the exit port, preferably by a distance that is no more than three times the diameter of the catheter body.

In the configuration where the balloon 160 extends axially on both sides of the exit port, the balloon 160 may completely surround the catheter body 162, with an opening formed therein over the exit port 158, or the balloon 160 may be attached along axial lines to the body 162 to avoid covering the exit port 158. Those of skill in the art will recognize that there are numerous constructions of a balloon attached to a catheter body that does not occlude a side port in the body.

With reference to the enlarged area of FIG. 6c shown in FIGS. 7A-7B, a tissue penetrator 164 is then advanced through a lumen in the catheter 156 so as to project from the exit port 158. By virtue of a sharp tip or other tissue penetrating means, the tissue penetrator 164 advances through the wall of the artery LAD, through any intervening tissue, and through the wall of the vein AIV into its lumen 166 upstream of the obstruction. Because the balloon 160 also contacts the wall of the LAD opposite the vein AIV, any reaction force transmitted to the catheter from resistance to tissue penetration is counteracted. That is, the balloon 160 maintains the position of the exit port 158 against the wall of the LAD, which helps the tissue penetrator 164 pass through the several layers of tissue. Furthermore, locating the exit port 158 against the wall of the LAD that is closest to the vein AIV reduces the distance that the tissue penetrator 164 must travel before entering the lumen 166.

Figure 6D:
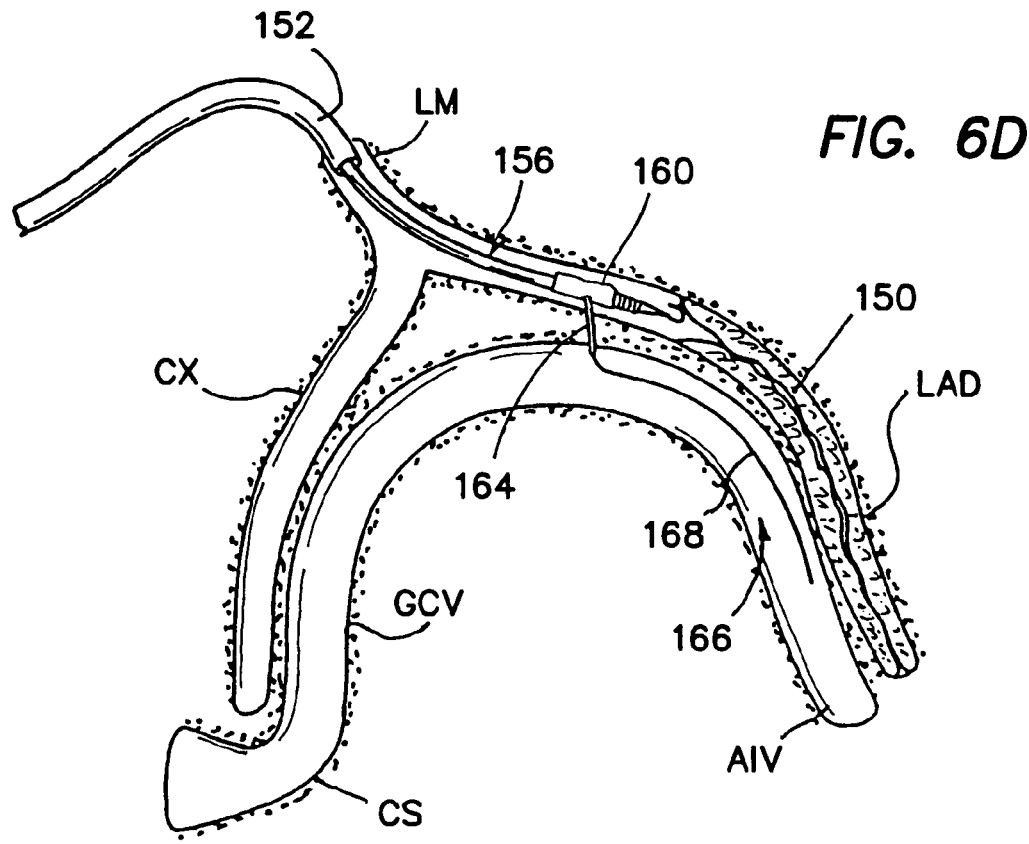

As shown in FIG. 6D, a first crossing guidewire 168 is advanced through a lumen of the tissue penetrator 164 and into the lumen 166 of the vein AIV. During this operation, the catheter 156 and the tissue penetrator 164 may be in the position shown in FIG. 6C with the balloon 160 inflated, or the balloon may first be deflated as seen in FIG. 6D. The tissue penetrator 164 is then retracted into the catheter 156 leaving the crossing guidewire 168 in place such that it extends from the lumen of the artery LAD into the lumen 166 of the vein AIV.

Figure 6E:
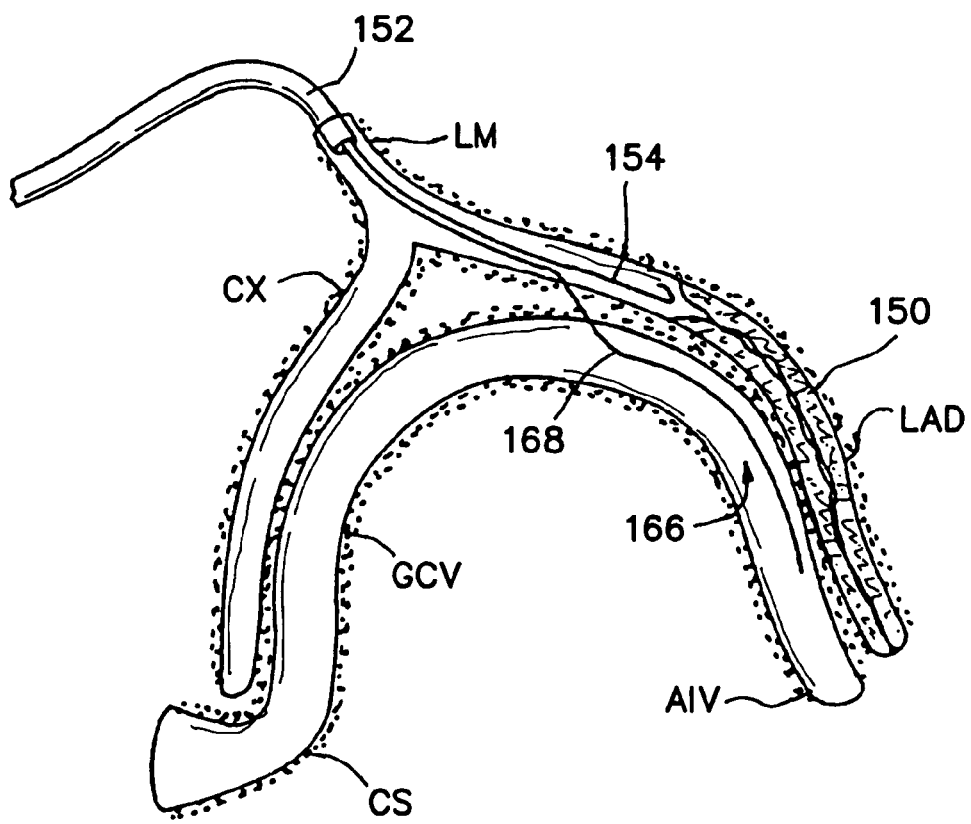

As shown in FIG. 6E, the catheter 156 is then removed by retracting it back over the primary guidewire 154 and out through the guide catheter 152 leaving the guidewires 154 and 168 in place.

Figure 6F:
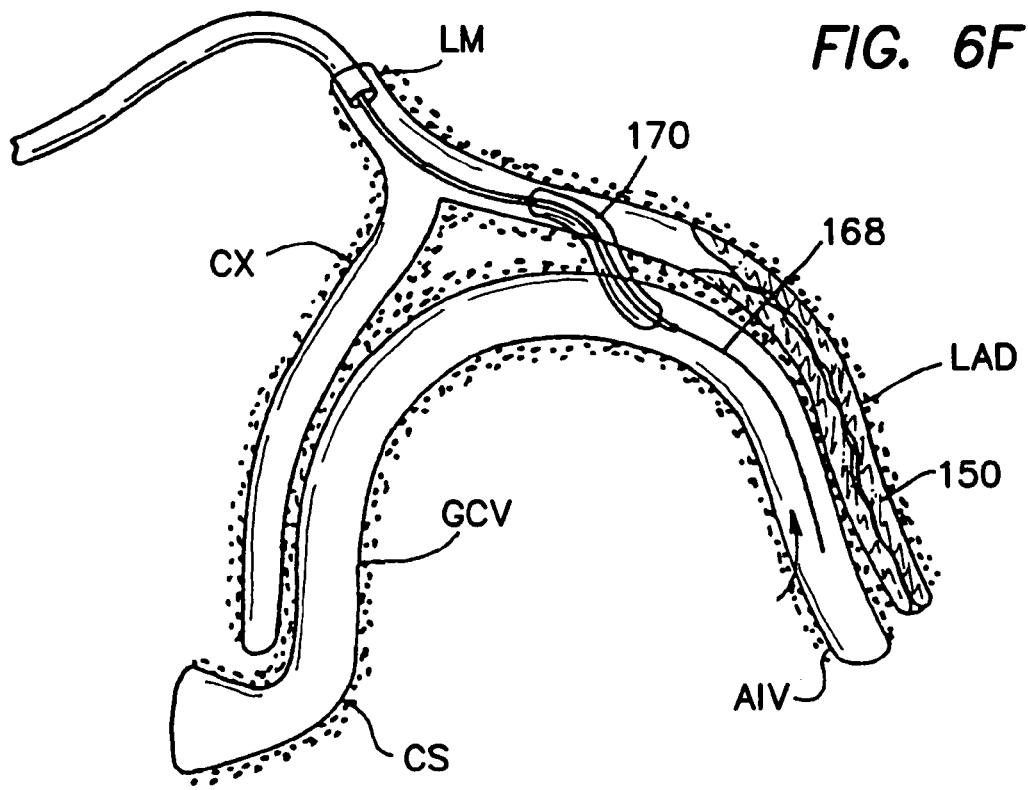

Thereafter, as shown in FIG. 6F, if it is necessary to enlarge or modify the penetration tract created by the penetrator 164, a tract modification or enlargement apparatus 170 may be advanced over the first crossing guidewire 168 to enlarge or otherwise modify the penetration tract. This tract modifying apparatus 170 may comprise a balloon catheter or radiofrequency tissue severing device as described in U.S. patent application Ser. No. 09/056,589, the entirety of which is expressly incorporated herein by reference.

Figure 6G:
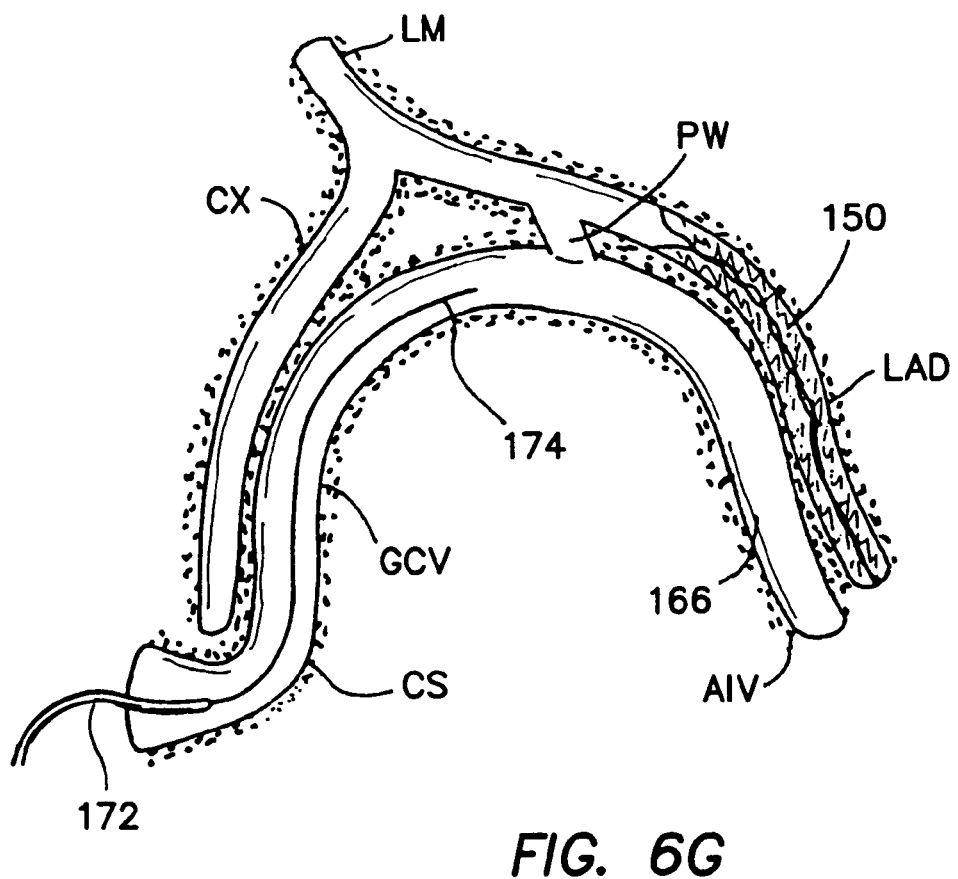

As shown in FIG. 6G, after any necessary enlargement or modification of the penetration tract has been complete, the tract modifying apparatus 170 and first crossing guidewire 168 are removed, leaving open the passageway PW between the artery LAD and vein GCV/AIV. Also, a catheter 172 is introduced into the coronary venous sinus CS and a guidewire 174 is advanced through the catheter 172 and into the vein GCV.

Figure 6H:
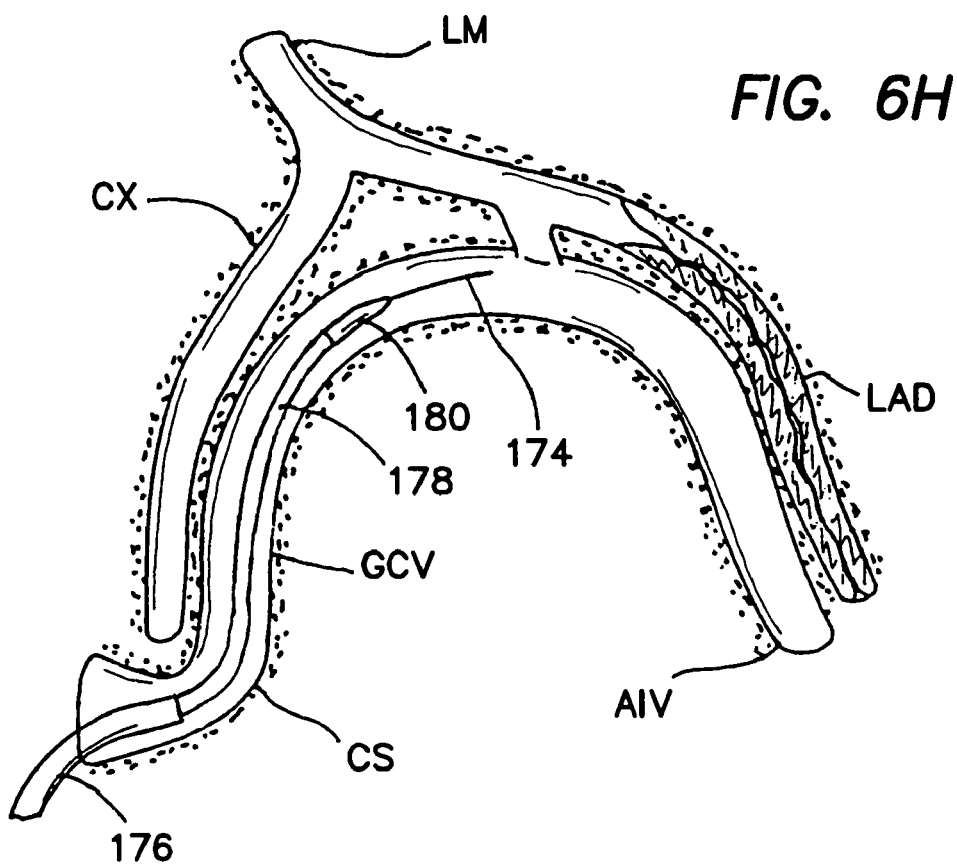

As shown in FIG. 6H, the catheter 172 is then removed and a coronary sinus guide catheter 176 is introduced over the guidewire 174 into the coronary venous sinus CS. A subselective sheath 178 and introducer 180 are then advanced together through the coronary sinus guide catheter 172, over the guidewire 168 and into the vein GCV proximal to the passageway PW. This coronary sinus guide catheter 176, subselective sheath 178 and introducer 180 may be of the type described in detail in U.S. patent application Ser. No. 09/282,276 entitled CATHETERS, SYSTEMS AND METHODS FOR PERCUTANEOUS IN SITU ARTERIO-VENOUS BYPASS, the entirety of which is expressly incorporated herein by reference.

Figure 6I:
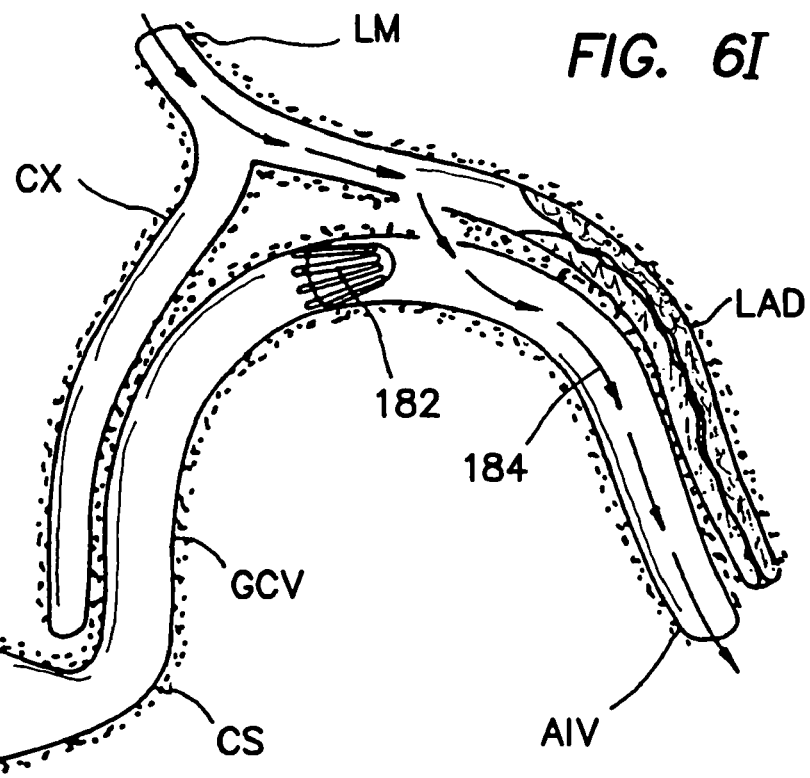

The introducer 180 is then removed leaving the subselective sheath 178 and guidewire 174 in place. Thereafter, as shown in FIG. 6I, an embolic blocker 182 is advanced through the subselective sheath 178 and implanted in the vein GCV proximal to the passageway. The subselective sheath 178, guidewire 174, and guide catheter 176 are then also removed from the body. This completes the PICVA procedure, allowing arterial blood to flow (see arrows 184) from the artery LAD, through the passageway PW and into the vein GCV/AIV where it flows in the direction opposite normal venous return so as to retro-perfuse the ischemic myocardium through the coronary vein(s).

Figure 8B:
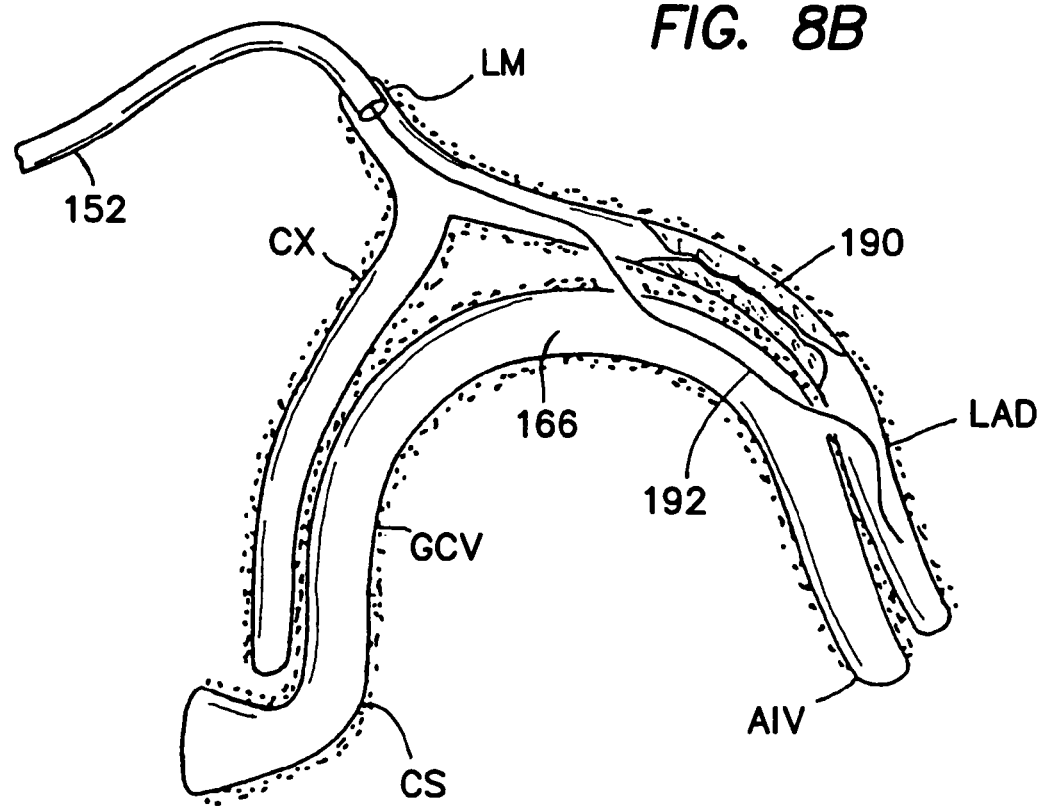
Figure 8C:
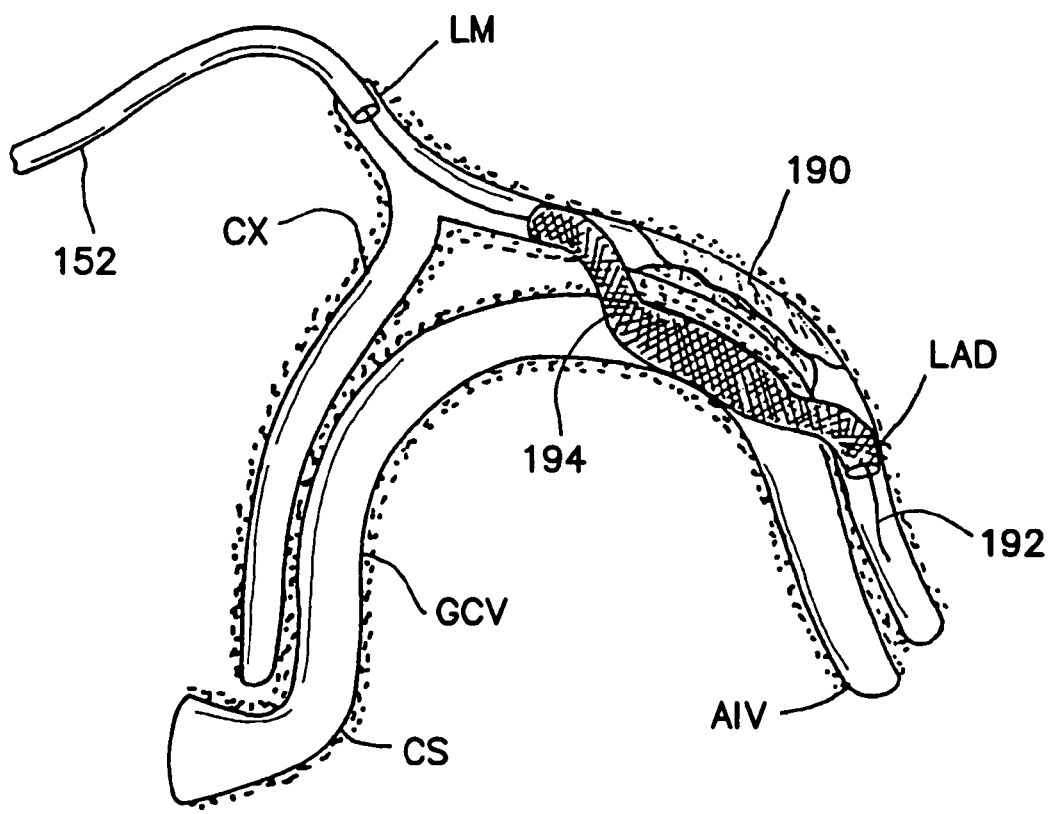

An Example of a PICAB Procedure Using a Stabilized Penetration Catheter:

FIGS. 8A-8C show, in step-by-step fashion, an example of the manner in which a two-channel Percutaneous In Situ Coronary Artery Bypass (PICAB) procedure may be performed, or in the alternative, how the above-described PICVA procedure (FIGS. 6A-6I) may be converted into a two-channel PICAB procedure. This PICAB procedure will typically be used in cases where an obstruction 190 does not extend into the distal LAD and thus, a patent distal LAD is available to carry blood flow to the ischemic myocardium.

If the two-channel PICAB technique is to be employed in lieu of the placement of the embolic blocker 182, shown in FIG. 6I in relation to the above-PICVA procedure (starting from the step referenced in FIG. 6F), the primary guidewire 154 is withdrawn and the tissue penetrating catheter 156 is advanced over the crossing guidewire 168 to the position shown in FIG. 8A. To accomplish this, the tissue penetrator 164 (FIG. 6D) is retracted over the crossing guidewire 168 to remove the first crossing guidewire from the tissue penetrator 164, and then the crossing guidewire 168 is introduced into a lumen (not shown) of the catheter 156, such as in an "over-the-rail" technique. Consequently, the catheter 156 can be advanced over the crossing guidewire 168 to the position of FIG. 8A wherein the catheter extends through the lumen of the artery LAD, through the openings created in the walls of the artery LAD and the vein AIV and into the lumen 166 of the vein AIV. The balloon 160 remains in a deflated state during this advancement. The longitudinal or axial position of the catheter 156 in the vein AIV relative to the obstruction 150 is monitored using conventional techniques.

With the catheter 156 in the position shown in FIG. 8A, an imaging device or system is again actuated and the catheter 156 is rotated within the vein AIV as required and as explained above in connection with FIG. 6B to cause the penetrator path indication, and exit port 158, to be aimed at the lumen of the artery LAD at a location downstream of the obstruction 190.

Subsequently, the catheter 156 is stabilized within the AIV at the location of the exit port 158 using any of the means described herein. Namely, as seen in FIGS. 8A and 9A-9B, the balloon 160 attached to the catheter 156 is inflated so as to press the exit opening 158 against the wall of the AIV closest to the target structure; in this case, the adjacent artery LAD.

With the penetrator path indication and the exit port 158 properly aimed at the artery LAD, and the catheter 156 stabilized within the vein AIV, the tissue penetrator 164 is advanced from the catheter 156 through the walls of the vein AIV and the artery LAD and into the lumen of the artery LAD as shown in FIGS. 8A and 9A-9B. Also, as shown, a second crossing guidewire 192 is advanced through the lumen of the tissue penetrator 164 and into the lumen of the artery LAD.

As shown in FIG. 8B, the tissue penetrator 164 is then retracted into the catheter 156, and the catheter 156 and the first crossing guidewire 168 are then removed leaving the second crossing guidewire 192 in place such that it extends from the artery LAD into the lumen 166 of the vein AIV and back into the distal artery LAD.

To create a blood flow channel around the obstruction 190, an expandable connector 194 may be employed. As shown in FIG. 8C, the connector 194 is implanted such that it extends from the artery LAD through the openings created in the walls of the artery LAD and the vein AIV, through the lumen 166 of the vein AIV, through the openings created in the walls of the vein and artery LAD distally of the obstruction 190 and back into the distal artery LAD. The expandable connector 194 may be implanted, for example, by advancing a connector delivery catheter (not shown) over the second crossing guidewire 192.

After implantation of the connector 194, the second crossing guidewire 192 is withdrawn and so is the guide catheter 152. It will be appreciated that instead of deploying one expandable connector, it may be preferred to employ two shorter connectors (not shown) at each of the first and second crossing sites. In this approach, a proximal and distal embolic blocker may be required to be placed in the vein proximal to the first crossing site (in the GCV) and distal to the second crossing site (in the AIV) to complete the bypass circuit.

Examples of Other Stabilizer Constructions and/or Functions:

As discussed here above, stabilizers other than balloons may be used for stabilizing the catheters of the present invention. Furthermore, even in catheters wherein balloon(s) are used for stabilization, the balloon(s) may be specifically configured and/or position to perform other functions (e.g, hemostasis, tamponade, providing imageable markers for facilitating orientation and positioning of the catheter, etc.) In this regard, FIGS. 2 and 10-12 to illustrate examples are of some additional or alternative modes of construction of the stabilizer to accomplish the desired stabilizing function and or additional other functions.

Figure 2:
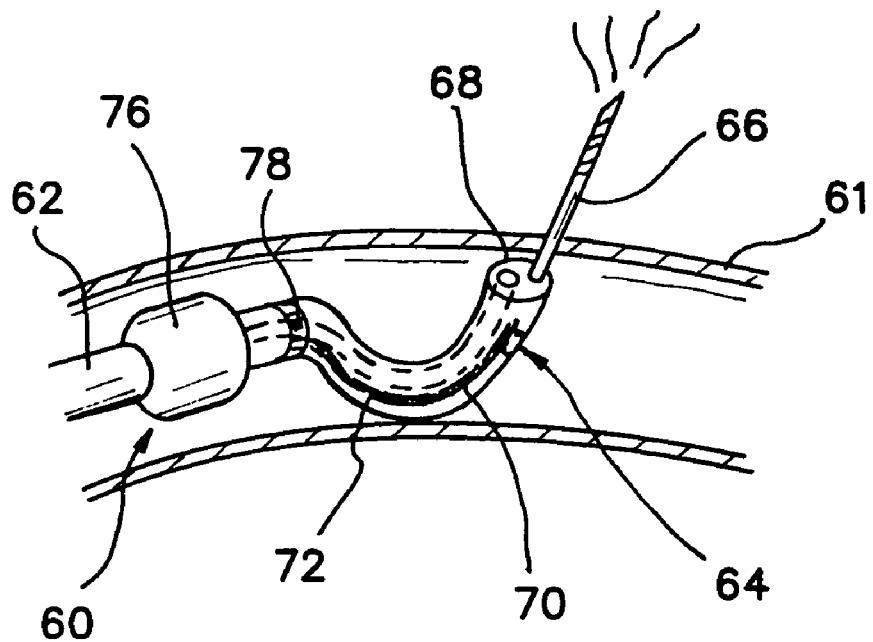
FIG. 2 is a sectional view through a blood vessel showing a penetration catheter of present invention having an actively deflectable tip for stabilizing a distal portion and a tissue penetrating element extending therefrom.

Specifically, FIG. 2 illustrates another embodiment of a TVIS catheter 60 in accordance with the present invention advanced into a predetermined location with a blood vessel 61. The catheter 60 includes an elongate, flexible body 62 terminating in a distal portion 64 from which a tissue penetrating element 66 projects. That is, the catheter 60 includes a lumen (not illustrated) through which the tissue penetrating element 66 translates, the lumen opening at a distal tip 68 of the catheter. Alternatively, the tissue penetrating element 66 may project through a side opening of the catheter.

The TVIS catheter 60 has an actively deflectable distal portion 64 by virtue of a shape memory material 70 embedded within the catheter body 62. When the initially straight shape memory material 70 is heated past a threshold temperature, such as through the use of a heating coil 72, it assumes a bent configuration as shown. In the bent configuration, the distal portion 64 contacts the wall of the blood vessel 61 opposite from the direction that the tissue penetrating element 66 is deployed. As a result, the distal portion 64 is stabilized within the blood vessel 61 to facilitate passage of the penetrating element 66 through any intervening tissue and into an adjacent body cavity, such as an adjacent blood vessel.

The catheter 60 may also be provided with a balloon 76 for further stabilization within the blood vessel 61. Additionally, a passive imaging marker 78 denoting the beginning of the distal portion 64 may be provided for external positioning of the catheter 60.

It should be appreciated by those of skill in the art, that there are various other ways to accomplish a deflecting tip to cause stabilization of the catheter 60 that do not require the shape memory material 70. A pull-wire (not shown) may be incorporated into or along side the catheter lumen and controlled from the proximal end which when activated will cause the catheter tip to assume a bent configuration similar to that illustrated in FIG. 2. A balloon, mounted on or near the catheter tip, that assumes a curved shape when inflated, will cause the same type of deflection when pressurized. In these deflecting tip embodiments, the amount of deflection will determine the trajectory of the tissue penetrating element 60 when deployed. A visualization element, such as a radiopaque marker (not shown) may be included to indicate the trajectory of the tissue penetrating element 60 and assist in rotational orientation of the catheter.

FIG. 10 shows a stabilized tissue penetrating catheter device 200 that may be used to form the initial penetration from a host vessel into a target location. The particular catheter device 200 shown in this example includes an elongated catheter body 202 having a proximal end 204, a distal end 206, a Catheter Distal Diameter CDD, a tissue penetrating member 208, a guidewire lumen 210, a balloon inflation lumen and a non-concentric stabilizer balloon 216 that extends away from the catheter body in a radial direction that is substantially opposite from the direction in which the tissue penetrating member 208 will extend when advanced from the catheter to attain a Stabilizer Diameter SD. (See dotted lines on FIG. 10) A handle/controller 218 is coupled to the proximal end 204 of the catheter body 202. A tissue penetrating member advancement/retraction knob 220 is formed on the handle and is useable to control the advancement and retraction of the tissue penetrating member.

In the embodiment of FIG. 10, the balloon 216 extends substantially to one side over the catheter body 202, radially opposite the location at which the tissue penetrating member 208 exits the catheter body. Optionally, and on-board imaging element 222, such as an ultrasound imaging transducer, may be located on or within the catheter body 202 to facilitate imaging of one or more markers on the catheter body and or the target location for the purpose of positioning and aiming the catheter device. Also optionally, an orientation marker 224 may be located on the balloon 216 at or near the location on the balloon that is farthest away from the catheter body 202 when the balloon is inflated. Such marker 224 may be imaged by an imaging apparatus, such as a fluoroscope ultrasound transducer, etc. located outside of the patient's body. Such externally located imaging device is initially positioned to image both the vessel in which the catheter body 202 is positioned and the target location (e.g., target vessel). Thereafter, the imaging device may be slowly moved until the distance between the images of the vessel in which the catheter body 202 is position and target location is maximized. Such maximization of the distance between the vessel in which the catheter body 202 is positioned and the target location as seen on the image, indicates that the image is being obtained from a vantage point that is on a line that is substantially normal to a plane that extends through both the resident vessel and the target. Thereafter, the balloon is inflated to a size that does not firmly coapt with the vessel wall but yet substantially fills the lumen of the vessel. With the balloon so inflated, the catheter body is rotated until the image of the balloon's marker 224 is at its maximum distance from the target. Because the marker 224 is located radially opposite the direction in which the tissue penetrating member 208 will expand, such positioning of the marker will indicate that the tissue penetrating member 208 is properly aimed at the target. Thereafter, the balloon may optionally be further inflated to rigidly coapt with and frictionally engage the vessel wall or it may be allowed to remain at its current state of inflation if such current state of inflation is deemed to provide adequate stabilization of the catheter for penetration. Thereafter, the tissue penetrator advancement/retraction knob 220 is advanced to cause the tissue penetrator 208 to pass laterally from the catheter body 202 and to the target location.

In embodiments where the catheter is inserted in opposite the direction of normal bloodflow, the radiopaque dye or contrast media may be injected through the guidewire lumen to determine whether or how much blood is passing the inflated balloon 216. In the other embodiments where the catheter is inserted in the same direction as normal bloodflow within the vessel, a separate contrast medium injection lumen and outlet port may be located proximal to the balloon 216 so that contrast medium may be injected upstream of the balloon for the purpose of determining whether or how much blood is flowing past the balloon. In this manner, the balloon may be precisely inflated to a desired diameter or cross section to provide the desired degree of occlusion of bloodflow through the vessel. As explained hereabove, in some applications it may be desired for the balloon to fully occlude bloodflow through the vessel for the purpose of providing hemostasis. In other applications, it may be desired for the balloon to be inflated only to a diameter or dimension that provides the desired stabilizing function but which does not fully coapt with the wall of the vessel, thereby allowing some bloodflow to pass the balloon. Moreover, in some applications, this aspect of the invention may be used to obtain a precise measurement all of the luminal diameter of the blood vessel so that stents, blockers, connectors or other implantable devices may be size-matched to the current luminal diameter of the vessel. The provision of lumens and or outlet ports for the injection of dye or radiographic contrast medium upstream of the balloon will permit such specific sizing of the inflated balloon to accomplish these purposes if desired during the particular procedure.

Optionally, flow-through channels such as elongate indentations or invaginations, may be formed in and extend longitudinally on the inflated balloon 226 to permits some blood to flow pass the balloon even in embodiments or applications where the balloon is fully inflated and in coaptation or engagement with the wall of the vessel.

FIG. 11 show was another tissue penetrating catheter device 230 that shares a number of elements in common with the tissue penetrating catheter device 200 of FIG. 10, but which incorporates a catheter body 202a having a tapered distal portion 202d and a stabilization/dilation balloon 232 formed on such tapered distal portion 202d. This particular tissue penetrating catheter device 230 is useable in vessels that are obstructed or narrowed. With the balloon 232 deflated, the tapered distal portion 202d of the catheter body 202a is advanced into the obstructed or narrowed portion of the vessel. The balloon 232 is then inflated to dilate the obstruction or narrowed region of the vessel. In this regard, the balloon 232 may be a noncompliant angioplasty balloon capable of performing the desired vessel dilation or angioplasty. It will be appreciated that for vessels that have substantially long, narrowed, or obstructed regions, the balloon may be initially inflated then deflated and the catheter may be advanced further, then the balloon may be inflated and deflated again. This procedure may be repeated a number of times to gain advancement of the catheter body 202a, 202d to the desired position within the narrowed or obstructed vessel. Thereafter, the balloon 224 may be inflated to a desired diameter to facilitate stabilize a shin of the catheter during advancement of the tissue penetrating member 208, as described hereabove. Optionally, the balloon 232 of this catheter device may also include an imageable orientation marker 224 of the type described hereabove.

Figure 12:
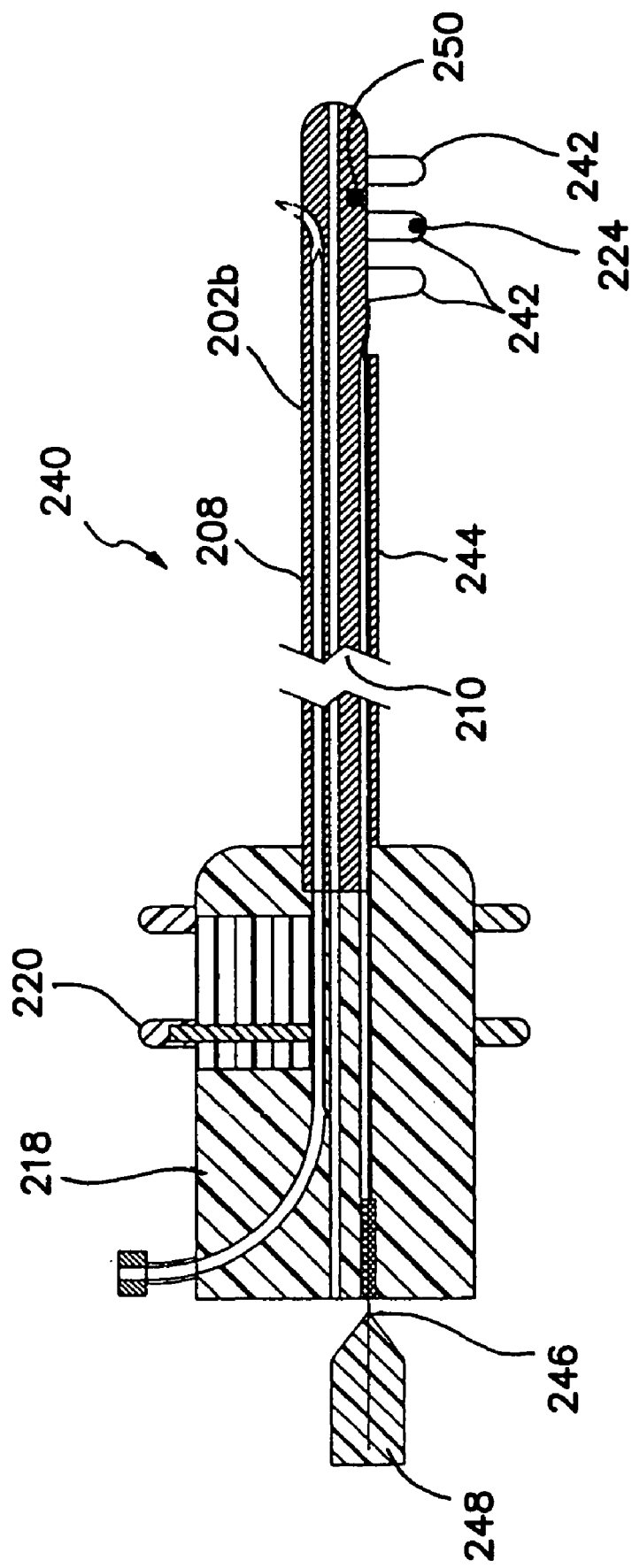
FIG. 12 is a longitudinal sectional view of an embodiment of a tissue penetrating catheter having a stabilizer that comprises a laterally deployable, substantially rigid member (e.g., a laterally extendable "foot").

FIG. 12 shows another alternative tissue penetrating catheter device 240 that shares the same basic elements or components in common with the catheters shown in FIGS. 10 and 11, but which incorporates a plurality of radially extendable stabilizer members 24 or feet in lieu of a balloon-type stabilizer. As shown, the radially extendable stabilizer members 242 are spring loaded or otherwise biased to a radially extended position shown in FIG. 12 whereby they extend laterally or radially outward from the catheter body 202b in a direction that is radially opposite (180 degrees from) the direction in which the tissue penetrating member 208 extends when advanced from the catheter body 202b. A control cable or wire 246 extends through an actuator lumen 244. The proximal end of the control wire 246 is attached to a stabilizer control knob 248 on the handle 218 and its distal end is connected to the radially extendable members 242. When it is desired for the radially extendable members 242 to be retracted within the catheter body, the control wire is pulled in the proximal direction to overcome the bias of the members 242 thereby pulling the members into the catheter body. The stabilizer control knob 248 may be locked in a retracted position whereby the stabilizer members 242 are maintained in their retracted positions (not shown) during insertion and advancement the catheter body 202b to the desired location. Thereafter, the stabilizer control knob 248 may be unlocked, advanced and the spring bias of the stabilizer members 242 will cause them to advance and assume their radially extended position. Optionally, an imageable orientation marker 224 of the type described hereabove and shown in FIG. 11 may be located at or near the outer-most end of one or all of the stabilizer members 242 to facilitate the desired rotational orientation and or longitudinal position of the catheter device and hanging of the tissue penetrating member 208. Also, optionally, any imaging element 250 such as any imaging transducer, marker or other imaging or imageable apparatus may be located on were into the device 240 for use in imaging the target location or for otherwise facilitating the desired longitudinal position, rotational orientation and or in lieu of the device 240.

Stabilizing member(s) of numerous other designs or types may also be used in accordance with this invention. For example, the catheter device may incorporate an expandable cage, member(s) or catheter-portion(s) that are radially expandable, projectable or otherwise moveable laterally outward from the catheter body to stabilize the catheter body within the vessel lumen. On example of an expandable cage comprises a mesh or woven cage that is formed on the catheter body opposite the location at which the tissue penetrating element exits the catheter, such cage being attached to a pull wire that extends through the catheter and being biased to a non-expanded, collapsed configuration, whereby it is substantially flush with the outer surface of the catheter body. When it is desired to stabilize the catheter, the pull wire is withdrawn, thereby causing the cage to shorten and expand radially outward in a direction opposite the direction in which the tissue penetrator will pass from the catheter body. The expanded cage will thereby stabilize the distal portion of the catheter body within the vessel lumen during the penetration procedure has been completed, the pull wire may be released, thereby allowing the cage to resiliently return to its non-expanded, collapsed configuration.

Examples of Other Types of Procedures that may be Performed Using the Stabilized Tissue Penetrating Catheters:

Those of skill in the art will appreciate that, in addition to the PICVA and PICAB procedures described hereabove, the stabilized tissue penetrating catheters of the present invention may be used to perform a variety of other procedures and functions.

For example, the stabilized tissue penetrating catheter may be used to perform the initial penetration step of a transjugular intrahepatic portosystemic shunt procedure (TIPS procedure) or a transjugular extrahepatic portosystemic shunt procedure (TEPS procedure).

The TIPS and TEPS procedures are non-surgical, transluminal, catheter-based alternatives to surgically performed shunts for patients that have liver cirrhosis and "portal hypertension" (increased blood pressure in the veins that normally drain the intestines and spleen). The most common causes of cirrhosis in the U.S. are chronic alcohol abuse and hepatitis (either from a viral infection or idiopathic cause). As a result of the portal hypertension, many patients develop bleeding varacies in their stomach and/or esophagus, or chronic fluid accumulation known as ascites. The TIPS or TEPS procedures can be used in patients with cirrhosis who: 1) have experienced bleeding from the stomach or esophagus, 2) have ascites that is poorly controlled with medication, or 3) are awaiting a liver transplant and experiencing life threatening gastrointestinal bleeding.

Specifically, the TIPS procedure involves the creation of a blood flow passageway within the liver to form a shunt connecting the portal vein with a hepatic vein. One or more stents may be typically placed in the passageway to maintain its patency. The shunt then allows the blood in the bowels and spleen to bypass the diseased liver on the way back to the heart.

Specifically, the TEPS procedure involves the creation of a blood flow passageway outside of the liver to form a shunt connecting the inferior vena cava with the portal vein. One or more stents are typically placed in the passageway to maintain its patency. As in the TIPS procedure, this extrahepatic shunt also allows the blood in the intestines and spleen to bypass the diseased liver on the way back to the heart.

Figure 13:
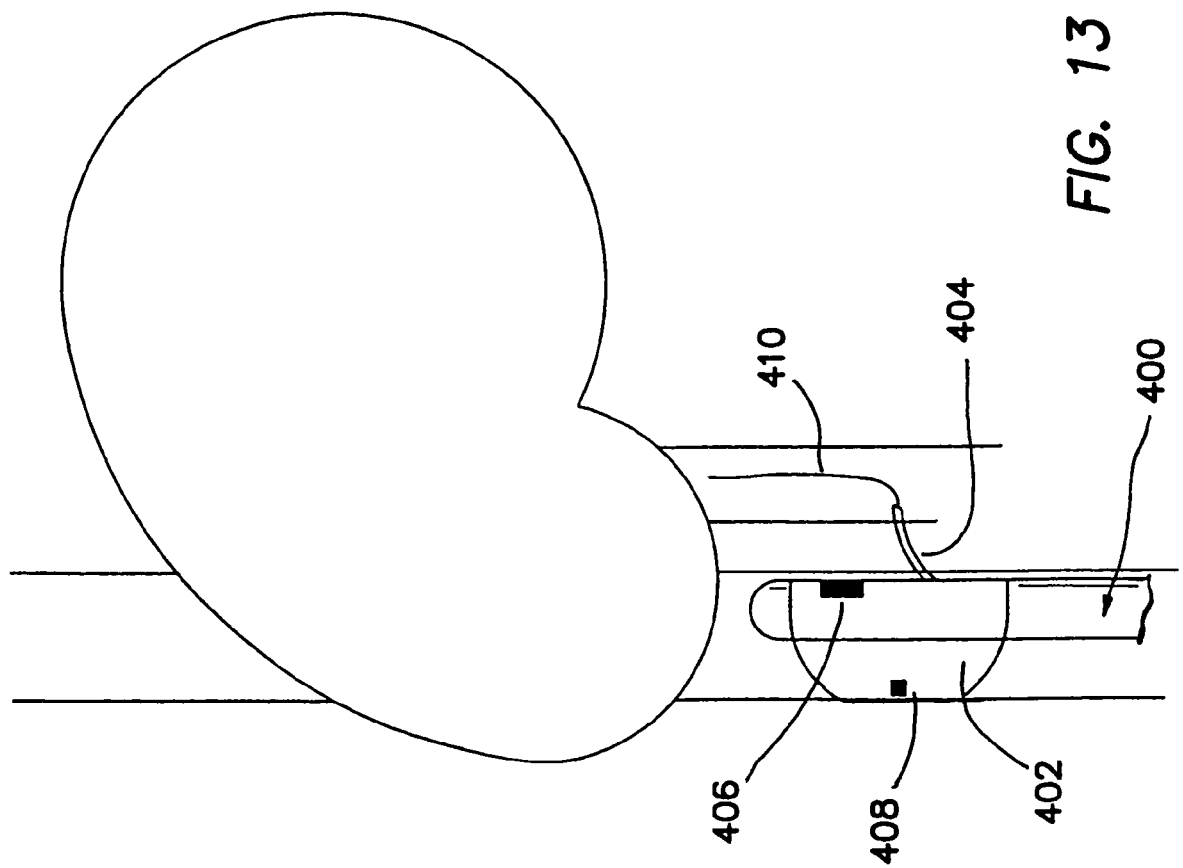
FIG. 13 is a schematic view of a stabilized tissue penetrating catheter of the present invention being used to perform the initial step of a transjugular extrahepatic portosystemic shunt procedure (TEPS procedure) for the treatment of liver cirrhosis and portal hypertension.

By way of example, FIG. 13 illustrates the initial step in performing a TEPS procedure wherein a stabilized tissue penetrating catheter device 400 of this invention is used to form an initial penetration tract from the inferior vena cava IVC to the portal vein PV. To accomplish this initial penetration step, a stabilized penetration catheter 400 of the present invention is advanced into the inferior vena cava IVC. The catheter 400 is longitudinally positioned at the location where the IVC-PV shunt is to be created. One or more radiopaque markers on the catheter or the infusion of a small amount of radio-dense contrast medium into the catheter's stabilizer balloon 402 may be used to facilitate and verify the proper longitudinal position a catheter by radiographic means. Thereafter, it is necessary to rotationally orient the catheter 400 such that the tissue penetrating member 404 will pass from the catheter 400, through the wall of the inferior vena cava IVC, through the wall of the portal vein PV and into the lumen of the portal vein PV, as shown. To facilitate this rotational orientation of the catheter 400, an optional imaging element 406 and may be provided on or within the catheter 400 to image the portal vein and possibly one or more penetrator-direction markers located on the catheter 400, for the purpose of aiming the tissue penetrating member 404 at the portal vein PV. The details of the manner in which the optional on-board orientation element 406 (which may be an ultrasound imaging transducer) and any marker(s) are used to accomplish the desired rotational orientation of the catheter 400 are fully described in U.S. Pat. No. 5,830,222 and PCT international publication Applications WO 98/16161, WO 98/46119, WO 99/49910 and WO 99/49793. Optionally, as an alternative to, or in addition to, any on-board orientation element, an imageable marker 402 may be formed on the balloon at or near the location on the balloon 408 that is radially farthest away from the catheter body when the balloon is inflated, and is also directly opposite (i.e., 180 degrees from) the direction in which the penetrator 404 will advance from the catheter 400. After the catheter 400 has been placed in its desired longitudinal position within the inferior vena cava IVC, the balloon 402 is inflated to a size that substantially fills the lumen of the inferior vena cava IVC but does not frictionally engage the wall of that vessel in a manner that would prevent the catheter 400 from being rotated. A fluoroscope or other imaging apparatus (e.g., ultrasound transducer) capable of imaging the marker 408 is positioned outside of the patient's body such that is can image both the inferior vena cava IVC wherein the catheter 400 is positioned and portal vein PV. Thereafter, the imaging device may be slowly moved until the distance between the IVC and PV images is maximized. Such maximization of the distance between the IVC and PV indicates that the imaged is being obtained from a vantage point that is located on a line that is substantially normal to a plane that extends through both the resident vessel and the target. Thereafter, the catheter 400 is rotated until the distance on the image between the marker 408 and the portal vein PV is maximized, thereby indicating that the tissue penetrating member 404, when subsequently advanced from the catheter 400, will pass into the portal vein PV as desired. With the catheter 400 so oriented, the stabilizing balloon 402 may optionally be further inflated to rigidly coapt with the wall of the inferior vena cava IVC, thereby pressing the opposite side of the catheter 400 (i.e., the side of the catheter 400 from which the tissue penetrating member 404 will exit) against the wall of the inferior vena cava IVC at a point closest to the adjacent wall of the portal vein PV and preventing further inadvertent rotation or movement of the catheter 400. Thereafter, the tissue penetrating member 404 is advanced from the catheter, through the wall of the inferior vena cava IVC, through the wall of portal vein PV and into the lumen of the portal vein PV, as shown. A guidewire 410 is then advanced through a lumen formed within the tissue penetrating member 404 and into the portal vein PV. Thereafter, the tissue penetrating member 404 may be retracted into the catheter 400 and the catheter may be removed, leaving the guidewire 410 in place. If necessary or desired, the initial penetration tract created by the use of the stabilized penetration catheter 400 may then be enlarged or dilated, stented or otherwise revised to provide the desired shunt for blood flow between the portal vein PV and inferior vena cava IVC.

Figure 14:
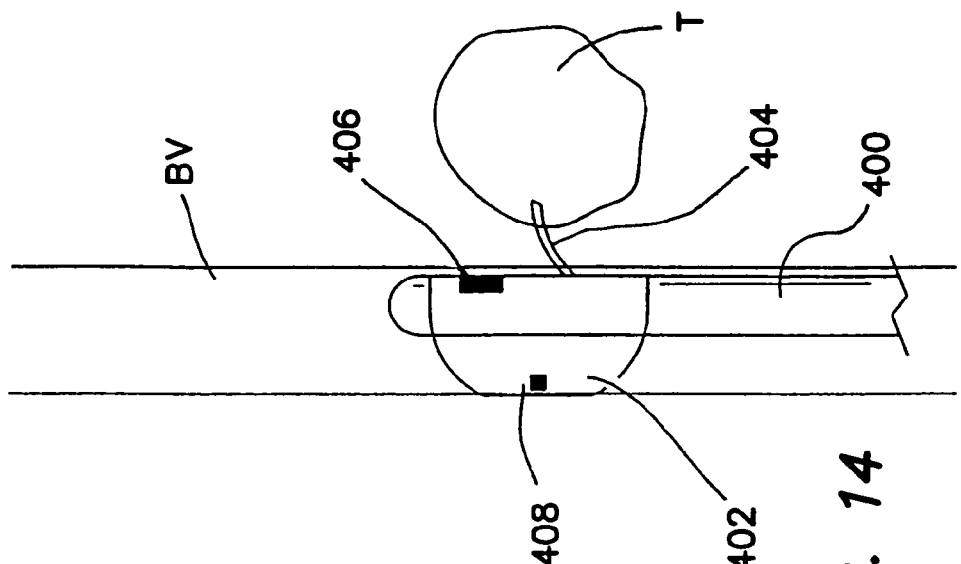
FIG. 14 is a schematic view of a stabilized tissue penetrating catheter of the present invention being used to deliver a drug or therapeutic substance to a target location (e.g., a tumor)

FIG. 14 illustrates the use of the catheter 400 shown in FIG. 13 and described in the immediately preceding paragraph, for the purpose of delivering a chemotherapeutic therapeutic agent, radiotherapeutic agent, or other therapeutic substance to a tumor T. In this example, the catheter 400 is advanced into a blood vessel BV and is positioned adjacent the tumor T. The optional imaging element 406 and/or marker 408 may then be used to rotationally orient the catheter in the manner described hereabove with respect to FIG. 13. After the catheter has been rotationally oriented within the blood vessel BV such that the tissue penetrating element 404 will pass directly into the tumor T, the stabilizing balloon 402 may be further inflated to rigidly engage the walls of the blood vessel BV thereby rigidly stabilizing and holding the catheter in its desired position and rotational orientation, and also thereby minimizing the distance that must be traveled by the tissue penetrating member 404 as it passes from the catheter into the tumor T. Thereafter, the tissue penetrating member 404 is advanced from the catheter, through the wall of a blood vessel BV and into the tumor T. The desired therapeutic agent or other therapeutic substance is then injected through a lumen (not shown) that extends longitudinally through the tissue penetrating member 404 and into the tumor T. After the desired therapeutic substance or agent has been injected into the tumor T, the tissue penetrating member 404 may be retracted back into the catheter 400 and the catheter may be removed. In some applications, the catheter 400 may be permitted to remain indwelling for a period of time to permit repeated dosing of the therapeutic agent or other substance to the tumor T, or a small tubular cannula may be passed through the lumen of the tissue penetrating member 404 and allowed to remain in place so that subsequent dosing may be made directly through that small cannula.

It is to be appreciated by those of skill in the art that the stabilized tissue penetrating catheters of the present invention may be used to perform other procedures where a connection between two anatomical structures is beneficial. Procedures which divert oxygenated blood around an obstruction may be performed not only in the heart, but also in the arms, legs and neck, such as a percutaneous carotid bypass. Connections between anatomical structures may be made to create a high flow condition, such as dialysis fistulas, and to relieve the pressure from excessive fluid such as hydrocephalic shunting. FIGS. 15a and 15b illustrate the manner in which the stabilizing balloon 402 or other stabilizer member may be used to accomplish a desired straightening of, or to impart rigidity to, a portion of the catheter 400 in addition to performing its stabilizing or anchoring function described hereabove. In FIG. 15a a catheter device 400 of the type shown in FIGS. 3 and 14 hereabove has been inserted into a curved blood vessel CBV such that the region of the catheter 400 between its imaging element 406 and the outlet aperture 405 through which the tissue penetrating member 404 will exit the catheter 400, is curved. In the particular embodiment illustrated in this example, the on-board imaging element 406 comprises an annular phased array ultrasound transducer or other suitable imaging device that provides an image within an image plane IP, such imaging plane IP being designated by dotted lines on FIGS. 15a and 15b. Also, the to tissue penetrating member 404 is specifically configured such, that so long as the portion of the catheter 400 between the imaging element 406 and outlet opening 405 is straight, the distal tip of the tissue penetrating member 404 will travel to and enter the imaging plane IP when the tissue penetrating member 404 is fully extended. However, as illustrated in FIG. 15a, if the portion of the catheter 400 between the imaging element 406 and the outlet aperture 405 is not straight, the distal tip of the tissue penetrating member 404 will not travel to and enter the imaging plane IP. Thus, in applications were the imaging element 406 is used for the purpose of imaging the target location TL and aiming the tissue penetrating member 404 at the target location TL, it is desirable to ensure that the portion of the catheter 400 between the imaging element 406 and outlet aperture 405 is straight so that the target location TL can be imaged properly by the imaging element 406 and further so that the penetrating member 404 will enter the target location TL as desired, when the tissue penetrating member 404 is fully extended. In FIG. 15a, the stabilizer or member or balloon 402 has not yet been deployed and, as shown, the portion of the catheter 400 between the imaging element 406 in the outlet aperture 405 is curved. This curvature of the catheter 400 results in the imaging plane IP being nonparallel to a transverse axis TA projected through the catheter at the location of the outlet aperture 405. As a result, when the target location TL is within the imaging plane IP, advancement of the tissue penetrating member 404 to its fully advanced position will not result in the distal tip of the penetrating member 404 entering the target location TL. However, as shown in FIG. 15B, when the stabilizing balloon or member 402 has been deployed, it will in addition to stabilizing the catheter 400 within the lumen of the curved blood vessel CBV the also impart rigidity to the region of the catheter 400 between the imaging element 406 and the outlet aperture 405, thereby straightening that portion of the catheter 400. Such straightening of that portion of the catheter results in the imaging plane IP being parallel to be transverse axis TA and ensures that when the target location TL is within the imaging plane IP, subsequent advancement of the tissue penetrating member 404 to its fully extended position will result in the distal tip of the tissue penetrating member 404 entering the target location TL as desired. In embodiments where the stabilizing member 402 (e.g., stabilizing balloon) is intended to rigidify or straighten the catheter in addition to stabilizing the location of the catheter within the vessel lumen, the stabilizer member 402 will be formed of material that is sufficiently rigid to accomplish such additional straightening function. In this regard, a stabilizing balloon that is intended to also straighten the catheter may be formed of non-compliant material of a type well known in the art of percutaneous transluminal balloon angioplasty and may be capable of being inflated to greater pressures than may be required of a stabilizer balloon 402 that is not intended to perform such additional catheter-straightening function.

Several of the above-described figures show catheters of the present invention whereon single or individual imageable markers are positioned at locations that are substantially opposite (i.e., 180 degrees opposed to) the outlet apertures through which the tissue penetrators exit the catheter bodies. Such imageable markers are intended for use in rotationally orienting the catheter such that the tissue penetrator will pass into the desired target location, when advanced.

Placement of a single imageable marker on the stabilization element allows the marker to be located at a greater distance from the rotational axis of the catheter than if the marker was placed on the catheter body itself. This greater radial distance correlates to increased movement of the market during the rotation of the catheter. This greater movement allows finer rotational control based on the visual feedback from the single marker as seen with such imaging technologies as fluoroscopy of ultrasound.

It is to be appreciated, however, that various other or more elaborate markers may be used to facilitate the desired rotational orientation of the catheter. Multiple marker schemes can also take advantage of the larger effective radius of the catheter including the stabilization element. Markers can be placed such that when then stabilization element is expanded, the markers have a greater separation between them than if the markers were placed on the catheter body alone. This greater separation between the markers, and between each marker and the rotational axis of the catheter, makers it easier to visually determine alignment of the markers as well as relative motion of the markers as the catheter is rotated.

Figure 16A:
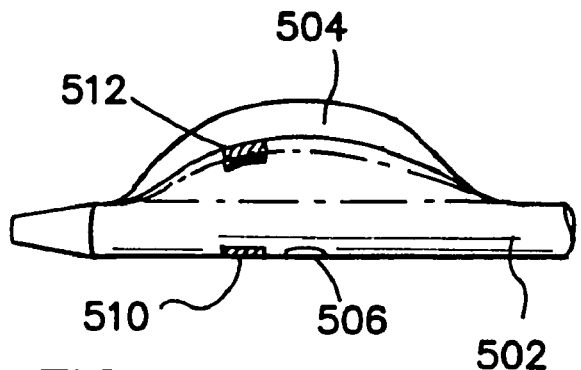
FIG. 16a is a partial side view of the catheter of FIG. 16.
Figure 16B:
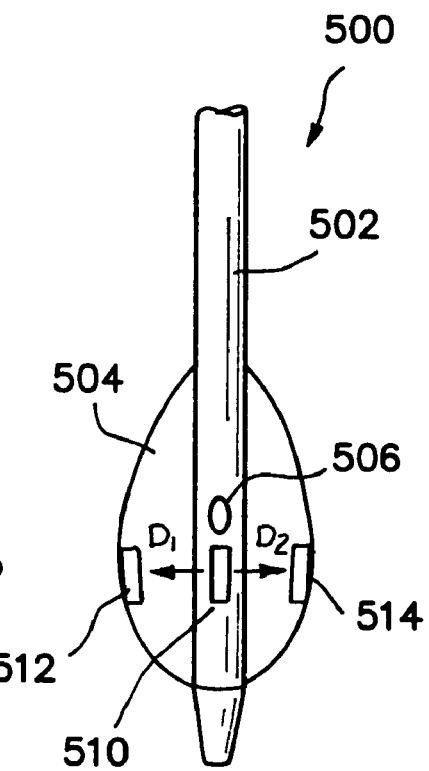
FIG. 16b is a partial top view of the catheter of FIG. 16.
Figure 16:
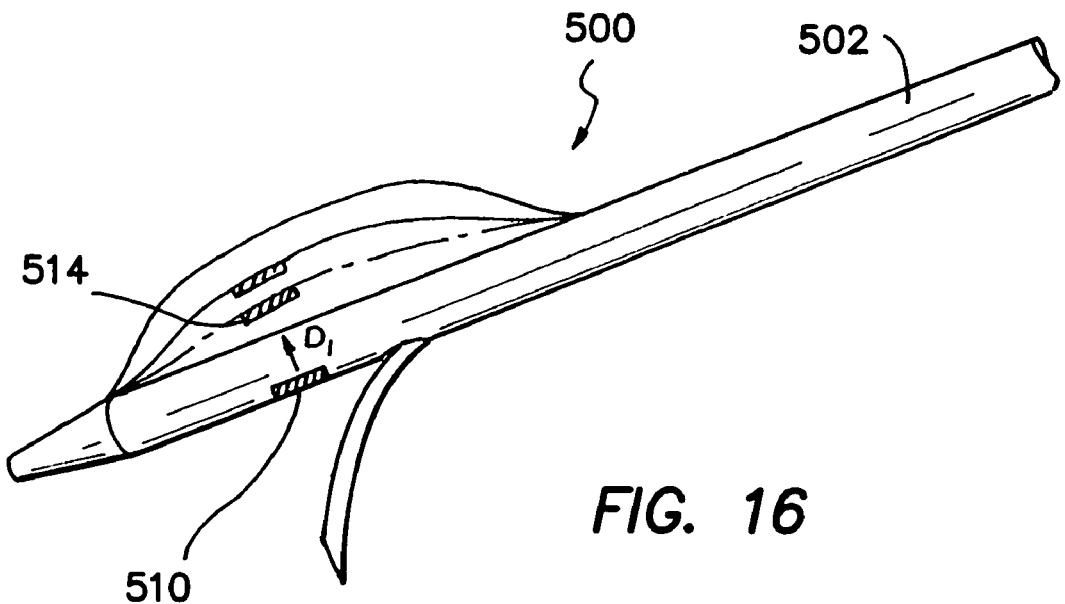
FIG. 16 is a perspective view of a stabilized tissue penetrating catheter of the present invention having a non-concentric balloon type stabilizer whereon a plurality of imageable markers are formed to facilitate rotational orientation of the catheter within a vessel such that the tissue penetrator is aimed at the target location.
Figure 16C:
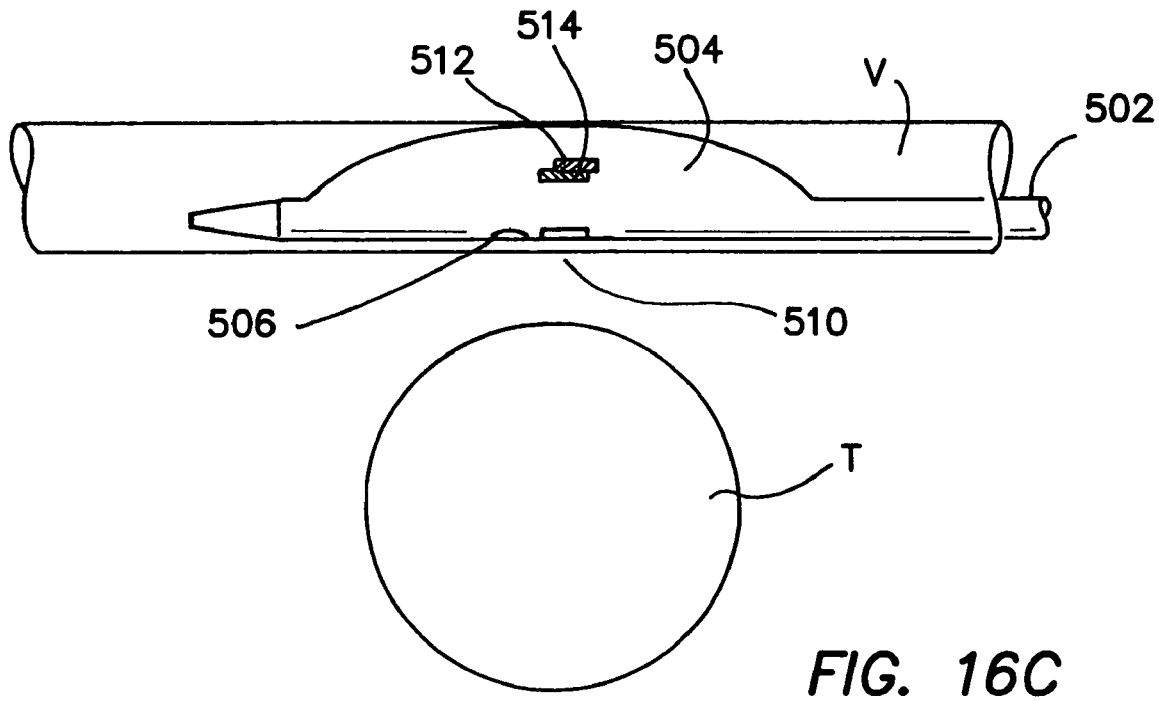
FIG. 16c is a schematic representation of an image showing the catheter of FIG. 16 in an incorrect rotational orientation.
Figure 16D:
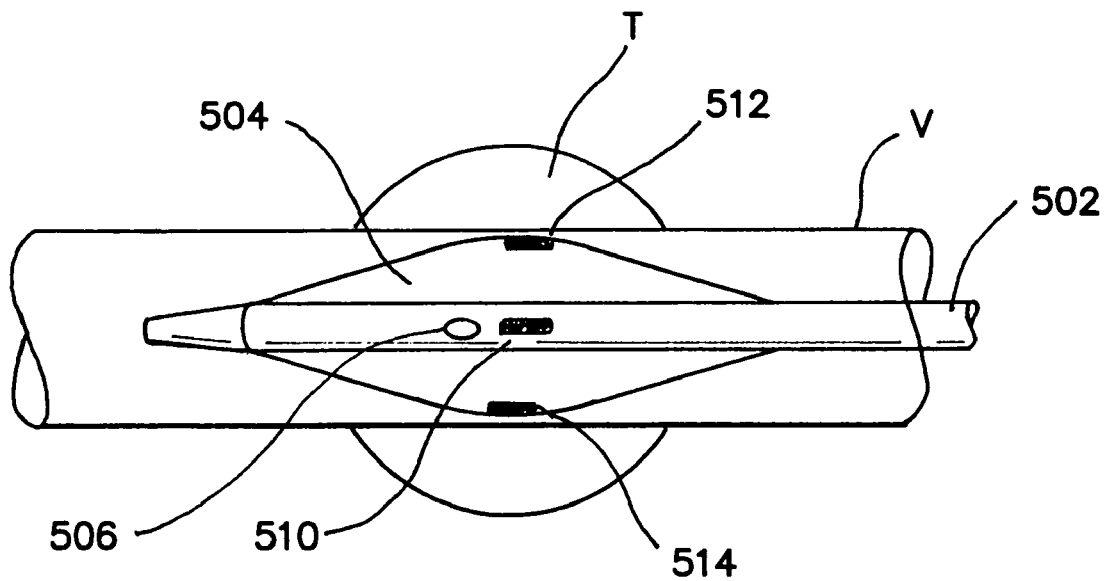
FIG. 16d is a schematic representation of an image showing the catheter of FIG. 16 in an incorrect rotational orientation.

One such marker scheme is shown in FIGS. 16a-16d which show a catheter 500 that comprises an elongate catheter body 502 having a nonconcentric balloon-type stabilizer 504 formed thereon opposite the exit aperture 506 through which the tissue penetrator 508 exits the catheter body 502. A first elongate imageable marker 510 is located immediately behind the outlet aperture 506 and is oriented in parallel with the longitudinal axis of the catheter. A second elongate imageable marker 512 is formed on one side of the balloon 504, at a first circumferential distance D1 from the first elongate imageable marker 506. A third elongate imageable marker 514 is formed on the other side of the stabilizer balloon 504, at a second circumferential distance D1 from the first elongate imageable marker 506, such second circumferential distance D2 being the same as the first circumferential distance D1. The catheter body 502 is inserted into a vessel and the balloon is inflated to a condition where it is substantially expanded but not so firmly in contact with the vessel wall as to prevent the catheter body form being rotated within the vessel. As shown in FIGS. 16c and 16d an imaging apparatus, such as a fluoroscope or ultrasound transducer located outside of the patients body, is used to obtain an image of the vessel in which the catheter is positioned and the target location TL (e.g., another vessel organ, tumor or location). The imaging apparatus is moved slowly until the distance between the vessel in which the catheter is positioned and the target location is maximized on the image (FIG. 16c). As shown in FIG. 16c, the second and third imageable markers will appear as separate, non-superimposed images on the image screen, when the catheter body 502 is not in its intended rotational orientation. (i.e., when the location at which the penetrator outlet opening 506 is not directly aligned with the target T). The catheter 500 is moved longitudinally until at least the first marker 510 indicates that the catheter body 502 is in the desired longitudinal position (e.g., when the first marker 510 is immediately adjacent the location where the penetration is to be formed). Thereafter, the catheter body 502 is rotated until the second and third markers 512, 514 become superimposed and appear as a single image on the image screen as shown in FIG. 16d. This indicates that the penetrator exit port 506 is directly aligned with the target T and when the penetrator is subsequently advanced, the penetrator will enter the target T as desired.

Although exemplary embodiments of the invention have been shown and described, many changes, modifications and substitutions may be made by those having ordinary skill in the art without necessarily departing from the spirit and scope of this invention. For example, various structures other than those disclosed herein may be used for stabilizing a tissue penetrating catheter within a blood vessel to facilitate advancement of a tissue penetrating element therefrom. Indeed, the present invention is intended to encompass any structure that contacts the inner wall of the host blood vessel to substantially maintain the radial position of the tissue penetrating catheter therein and resist any reaction forces imparted to the catheter via the tissue penetrating element. Those of skill in the art will understand that in addition to the various balloons and other stabilizing structure described herein, a non-inflatable mechanical structure may also be used to stabilize the tissue penetrating catheter. Furthermore, the expandable structure needed only contact the wall of the blood vessel in a manner that substantially resists catheter movement from the tissue penetrating reaction forces. Although various embodiments disclosed herein contact the wall of the blood vessel directly opposite from the direction that the tissue penetrating element objects, other structure may be deployed to service the same purpose. For instance, a pair of expandable legs may extend in a V-shape so as to contact the blood vessel wall generally opposite the direction that the tissue element projects, if not directly opposite that direction. Accordingly, it is intended that all such additions, deletions, modifications and variations be included within the scope of the following claims.

The invention claimed is:

1. A catheter device for penetrating through the wall of a vessel within a patients body to a target location outside of that vessel, said device comprising:
   a catheter body having a proximal end and a distal end, the catheter body being advanceable into the vessel;
   a tissue penetrator that is passable from the catheter body, through the wall of the vessel and to the target location outside the vessel;
   catheter orientation apparatus comprising at least one of i) an imageable marker indicative of the direction in which the tissue penetrator will pass from the catheter body and ii) an imaging apparatus for imaging at least the target location prior to passage of the tissue penetrator from the catheter body; and,
   a stabilizer that is radially extendable from the catheter body to deter at least some movement of the catheter body within the vessel as the penetrator penetrates through the wall of the blood vessel.

2. The catheter of claim 1, wherein the stabilizer is expandable.

3. The catheter of claim 2, wherein the stabilizer comprises an apparatus selected from the group consisting of:
   at least one balloon;
   at least one cage structure that is deployable laterally from the catheter body;
   at least one member that is deployable laterally from the catheter body; and,
   a portion of the catheter body that is initially in a first non-stabilizing configuration and is subsequently transitionable to a stabilizing configuration.

4. The catheter of claim 3, wherein the stabilizer expands concentrically about the catheter body.

5. The catheter of claim 4, wherein the stabilizer is located within a distance no greater than about three times the diameter of the catheter from a location at which the penetrator exits the catheter body.

6. The catheter of claim 4, wherein the stabilizer substantially surrounds a location at which the penetrator exits the catheter body and wherein a penetrator passageway is formed in the stabilizer to permit the tissue penetrator to pass therethrough.

7. The catheter of claim 3, wherein the stabilizer expands non-concentrically about the catheter body such that a location at which the penetrator exits the catheter body is located closely adjacent to or in contact with the blood vessel wall when the stabilizer is expanded.

8. The catheter of claim 7, wherein the stabilizer extends axially on both sides of a location at which the penetrator exits the catheter body.

9. The catheter of claim 1, wherein the stabilizer device comprises a shape memory alloy element that is initially disposed in a first configuration whereby the stabilizer is not deployed and is subsequently transitionable to a second configuration whereby the stabilizer is deployed.

10. The catheter of claim 1, wherein the stabilizer comprises at least two stabilizer members provided on the catheter, at least one of said stabilizer members being proximal to and at least one of said stabilizer members being distal to a location at which the penetrator exits the catheter body.

11. The catheter of claim 1, wherein the stabilizer is further constructed to straighten a portion of the catheter body when the stabilizer is deployed.

12. The catheter of claim 1, wherein the stabilizer is constructed and deployed in a manner that allows some body fluid to flow through the vessel, past the stabilizer, when the stabilizer is deployed.

13. The catheter of claim 1 wherein the orientation apparatus comprises at least one penetrator direction marker is formed on the stabilizer, said at least one penetrator direction marker being useable in conjunction with an imaging device, to orient the catheter body within the vessel such that the penetrator will pass into the target location.

14. The catheter of claim 13 wherein the penetrator direction marker is formed on the stabilizer at a location that is radially opposite the location at which the penetrator passes from the catheter body.

15. The catheter of claim 13 wherein the at least one penetrator direction marker is imageable by an imaging apparatus positioned outside of the patient's body.

16. The catheter of claim 13 wherein the at least one penetrator direction marker is imageable by an imaging apparatus positioned on or in the catheter.

17. The catheter of claim 16 wherein the orientation apparatus of the catheter further comprises a lumen for receiving an imaging apparatus therewithin such that the imaging apparatus may image the target location and at least on penetrator direction marker.

18. The catheter of claim 16 wherein the orientation apparatus of the catheter comprises an imaging apparatus mounted in the catheter, said imaging apparatus being useable to image the target location and at least on penetrator direction marker.

* * * * *